(12) United States Patent
Yang et al.

(10) Patent No.: US 12,171,858 B2
(45) Date of Patent: Dec. 24, 2024

(54) **PEPTIDE FOR TREATING SEPSIS DERIVED FROM RV2626C PROTEIN OF *MYCOBACTERIUM TUBERCULOSIS***

(71) Applicant: INDUSTRY-UNIVERSITY COOPERATION FOUNDATION HANYANG UNIVERSITY ERICA CAMPUS, Gyeonggi-do (KR)

(72) Inventors: Chul-Su Yang, Gyeonggi-do (KR); Sun Young Kim, Gyeonggi-do (KR)

(73) Assignee: INDUSTRY-UNIVERSITY COOPERATION FOUNDATION HANYANG UNIVERSITY ERICA CAMPUS, Gyeonggi-Do (KR)

( * ) Notice: Subject to any disclaimer, the term of this patent is extended or adjusted under 35 U.S.C. 154(b) by 392 days.

(21) Appl. No.: 17/515,800

(22) Filed: Nov. 1, 2021

(65) Prior Publication Data
US 2022/0218583 A1  Jul. 14, 2022

(30) Foreign Application Priority Data
Nov. 2, 2020  (KR) ........................ 10-2020-0144321

(51) Int. Cl.
| | |
|---|---|
| *A61K 8/64* | (2006.01) |
| *A23L 33/18* | (2016.01) |
| *A61K 38/07* | (2006.01) |
| *A61K 38/08* | (2019.01) |
| *A61P 35/00* | (2006.01) |
| *C07K 5/10* | (2006.01) |
| *C07K 7/06* | (2006.01) |
| *C07K 7/08* | (2006.01) |
| *C07K 14/47* | (2006.01) |

(52) U.S. Cl.
CPC ................ *A61K 8/64* (2013.01); *A23L 33/18* (2016.08); *A61K 38/07* (2013.01); *A61K 38/08* (2013.01); *A61P 35/00* (2018.01); *C07K 5/10* (2013.01); *C07K 7/06* (2013.01); *C07K 7/08* (2013.01); *C07K 14/4702* (2013.01); *C07K 2319/00* (2013.01)

(58) Field of Classification Search
CPC .......... A61K 8/64; A61K 38/07; A61K 38/08; A23L 33/18; A61P 35/00; C07K 5/10; C07K 7/06; C07K 7/08; C07K 14/4702; C07K 2319/00
See application file for complete search history.

(56) References Cited

FOREIGN PATENT DOCUMENTS

WO  WO-2009039854 A2 *  4/2009  ......... A61K 39/0011

OTHER PUBLICATIONS

Yan (Year: 2004).*
KR20120119560A, , Machine Translation (Year: 2012).*
Gao (Year: 2015).*
Alfthan (Year: 1995).*
Reid (Year: 2004).*

* cited by examiner

*Primary Examiner* — Jeffrey S Lundgren
*Assistant Examiner* — Ibrahim D Bori
(74) *Attorney, Agent, or Firm* — Armstrong Teasdale LLP

(57) ABSTRACT

The present invention relates to a use of a peptide containing an amino acid sequence represented by SEQ ID NO: 1 derived from the Rv2626c protein of *Mycobacterium tuberculosis* for treating sepsis. The peptide is excellent in inhibiting the inflammatory response induced by macrophages and is excellent in inhibiting the increase in the number of bacterial colonies, and thus can be usefully used for the treatment of sepsis.

11 Claims, 41 Drawing Sheets
Specification includes a Sequence Listing.

CPP-GG-Tuftsin-GG-Rv2626c CBS2 (123-131)

Vehicle         GRKKRRQRRRPQ-GG-(TKPR)$_{10}$
Rv2626c-CA  GRKKRRQRRRPQ-GG-(TKPR)$_{10}$-GG-(LPEHAIVQF)$_5$
Rv2626c-DN  GRKKRRQRRRPQ-GG-(TKPR)$_{10}$-GG-(LPQQAIVQF)$_5$

PEPTIDE FOR TREATING SEPSIS DERIVED FROM RV2626C PROTEIN OF *MYCOBACTERIUM TUBERCULOSIS*

CROSS-REFERENCE TO RELATED APPLICATION

This application claims the benefit of Korean Patent Application No. 10-2020-0144321 filed on Nov. 2, 2020, in the Korean Intellectual Property Office, the entire disclosure of which is incorporated herein by reference for all purposes.

BACKGROUND

1. Field of the Invention

One or more example embodiments relate to a use of a peptide containing an amino acid sequence represented by SEQ ID NO: 1 derived from the Rv2626c protein of *Mycobacterium tuberculosis* for treating sepsis.

2. Description of the Related Art

Bacterial antigens trigger an interaction between the host immune defenses and the mechanisms that allow the bacteria to escape from, or protect themselves from, host immunity. This host-pathogen interaction is highly complicated by intracellular pathogens, such as *Mycobacterium tuberculosis* (MTB), which is a cause of tuberculosis. *Mycobacterium tuberculosis* antigen, Rv2626c, is the most strongly expressed protein under stress conditions caused by exposure to hypoxia and nitric oxide (NO), and was also identified in the culture filtrate and lysate, and was observed to be highly expressed in activated macrophages and lungs. Rv2626c elicits a strong serum antibody response in patients with *Mycobacterium tuberculosis* and is thought to be important in immune profiling of disease states. However, the role of Rv2626c plays has not been elucidated yet. Understanding the interrelationship between macrophages and Rv2626c is important for the development of effective tuberculosis treatment. Sepsis is defined as life-related organ dysfunction resulting from an uncontrolled host response to infection. In sepsis, the immune response initiated by the pathogen does not maintain homeostasis, and excessive inflammation and bacterial proliferation continue to cause a pathological syndrome. The mortality rate of sepsis is close to 25%, and due to its high incidence and mortality, the expenditure therefor is significant worldwide. Although the level of understanding of the pathogenesis of sepsis has increased, the target treatment method is still insufficient.

Peptides and proteins have great potential as therapeutic agents. Currently, small molecule drugs of small size occupy most of the pharmaceutical market. Compared to typical small molecule drugs as such, peptides and proteins may be selectively used because there are many sites that meet the target. In addition, increased selectivity of peptides and proteins may reduce side effects and toxicity. Although peptides and proteins for therapeutic purposes are being continuously studied, methods to increase systemic stability and delivery to specific sites are being discussed. In addition, the lack of target specificity of cell penetrating peptides remains a major obstacle in clinical development.

Under such circumstances, the present inventors have completed the example embodiments by identifying that the *Mycobacterium tuberculosis* Rv2626c-derived peptide has anti-inflammatory activity, and that the conjugate of the peptide, cell penetrating peptide and macrophage target peptide has excellent sepsis therapeutic activity.

SUMMARY

The present invention provides a use of a peptide containing an amino acid sequence represented by SEQ ID NO: 1 derived from Rv2626c of *Mycobacterium tuberculosis* for treating sepsis.

Technical tasks to be achieved by the present invention are not limited to the aforementioned technical tasks, and other technical tasks, which are not mentioned herein, will be clearly understood from the following description by those skilled in the art.

According to an aspect, there is provided a peptide for treating sepsis containing or consisting of an amino acid sequence represented by SEQ ID NO: 1.

Sepsis refers to a condition in which systemic organ dysfunction occurs due to an abnormal inflammatory response to infection. Since the immune response initiated by microbial infection does not maintain homeostasis, and excessive inflammation and microbial growth persist, it is important to suppress inflammation and inhibit microbial growth.

The amino acid sequence represented by SEQ ID NO: 1 (LPEHAIVQF) is a sequence derived from the CBS2 domain of a *Mycobacterium tuberculosis* Rv2626c protein, and according to one embodiment of the present invention, it exhibits anti-inflammatory and sepsis therapeutic activity.

Specifically, the present inventors found that the CBS2 domain of the Rv2626c protein directly binds to the RING domain (N-terminus) of TRAF6 (TNF receptor-associated factor 6) to inhibit the TLR4 immune response by preventing lysine 63-ubiquitination of TRAF6. In addition, the present inventors found that the amino acid sequence represented by SEQ ID NO: 1 summoned macrophage in the process of removing bacteria during sepsis progression, and improved phagocytosis and differentiation into M2 macrophages.

According to one specific example of the present invention, the peptide for treating sepsis has excellent sepsis treatment effect when the sequence of SEQ ID NO: 1 is included repeatedly. Accordingly, the peptide for treating sepsis may include an amino acid sequence represented by SEQ ID NO: 1 repeated 1 to 15 times, preferably 3 to 12 times, and more preferably 5 to 10 times, or may consist of an amino acid sequence in which the amino acid sequence represented by SEQ ID NO: 1 is repeated. For example, the peptide for treating sepsis may include or consist of the amino acid sequence represented by SEQ ID NO: 1 repeated 10 times.

According to one specific example of the present invention, the peptide for treating sepsis may further include a cell penetrating peptide at an N-terminus of the amino acid sequence represented by SEQ ID NO: 1 in order to increase the cell permeability of the peptide.

The cell penetrating peptide (CPP) may be selected from the group consisting of HIV-TAT (SEQ ID NO: 3), TAT (SEQ ID NO: 5), dNP2 (SEQ ID NO: 6), VP22 (SEQ ID NO: 7), MPG (SEQ ID NO: 8), PEP-1 (SEQ ID NO: 9), EB1 (SEQ ID NO: 10), transportan (SEQ ID NO: 11), p-Antp (SEQ ID NO: 12), hCT (18-32) (SEQ ID NO: 13), KLA (SEQ ID NO: 14) and oligoarginine (SEQ ID NO: 15). For example, an HIV-TAT sequence (GRKKRRQRRRPG; SEQ ID NO: 3) may be used. The HIV-TAT sequence is a sequence derived from human immunodeficiency virus-1, and amino acids having a positive charge are present at a high frequency.

In addition, the peptide for treating sepsis may be a fusion peptide in which a tuftsin peptide (SEQ ID NO: 2) is linked to one end of the amino acid sequence represented by SEQ ID NO: 1. The tuftsin peptide is a macrophage-targeting peptide, and the macrophage-targeting peptide refers to a peptide capable of regulating macrophage activity by binding to a specific receptor on the surface of a macrophage. The tuftsin is a tetrapeptide consisting of four amino acid sequences, derived from the heavy chain Fc domain of immunoglobulin G, and is known to have an immunostimulatory effect.

According to one specific example of the present invention, the tuftsin peptide may be included in the peptide for treating sepsis in the form of repeating 1 to 20 times, preferably 5 to 15 times, and more preferably 7 to 12 times. In one example of the present invention, the tuftsin sequence was repeated 5 times and was included in the peptide for treating sepsis.

According to one specific example of the present invention, the peptide for treating sepsis may be in the form of a fusion peptide (CP-CBS2-Tuftsin) in which a cell penetrating peptide, an amino acid sequence represented by SEQ ID NO: 1 and a tuftsin peptide are sequentially linked, or a fusion peptide (CP-Tuftsin-CBS2) in which a cell penetrating peptide, a tuftsin peptide and an amino acid sequence represented by SEQ ID NO: 1 are sequentially linked.

According to one specific example of the present invention, each of the cell penetrating peptide, the amino acid sequence represented by SEQ ID NO: 1, and the tuftsin peptide are linked to one another with a peptide linker, and the peptide linker may be selected from the group consisting of GG (SEQ ID NO: 16), (GGGGS)n (n=1-5) (SEQ ID NO: 17) and (EAAAK)n (n=1-5) (SEQ ID NO: 18). In an example of the present invention, GG (SEQ ID NO: 16) was used as the peptide linker.

According to one specific example of the present invention, a cell penetrating peptide, a tuftsin peptide linked to the C-terminus of the cell penetrating peptide, and a fusion peptide (rRV2626c-CA) containing the amino acid sequence represented by SEQ ID NO: 1 linked to the C-terminus of the tuftsin peptide are remarkably excellent in the inflammatory response inhibitory effect and bacterial colony formation inhibitory effect in sepsis-induced mice without cytotoxicity. In particular, rRV2626c-CA exhibited an $IC_{50}$ value that was 250 times (in vitro) or 1000 times (in vivo) superior to rRV2626c-WT (CPP-CBS2).

The peptide for treating sepsis of the present invention may be administered parenterally during clinical administration and may be used in the form of general pharmaceutical preparations. Parenteral administration may refer to administration via routes other than oral, such as rectal, intravenous, peritoneal, intramuscular, arterial, transdermal, nasal, inhalation, ocular and subcutaneous. When the peptide for treating sepsis of the present invention is used as a pharmaceutical product, it may additionally contain one or more active ingredients exhibiting the same or similar function.

In other words, the peptide for treating sepsis of the present invention may be administered in various parenteral formulations. When formulated, the peptide is prepared by using generally used diluents or excipients such as fillers, extenders, binders, wetting agents, disintegrating agents and surfactants. Formulations for parenteral administration include sterilized aqueous solutions, water-insoluble excipients, suspensions, emulsions, lyophilized preparations, and suppositories. As water-insoluble excipients and suspensions, propylene glycol, polyethylene glycol, vegetable oil such as olive oil, injectable ester such as ethyl olate, and the like may be used. As base materials of suppositories, witepsol, macrogol, tween 61, cacao butter, laurinum, glycerogelatin, and the like, may be used.

In addition, the peptide for treating sepsis of the present invention may be mixed with many pharmaceutically acceptable carriers such as physiological saline or organic solvent. In addition, carbohydrates such as glucose, sucrose or dextran, antioxidants such as ascorbic acid or glutathione, chelating agents, low molecular proteins or other stabilizers may be used as pharmaceuticals to enhance stability or absorptiveness.

The peptide for treating sepsis of the present invention may be administered to a patient in the form of bolus, by single dose having relatively short period of infusion or by multiple doses for a long term. The dosage form and period are determined by considering various factors such as the age and health condition of the patient as well as the route of administration of drugs and the number of treatments. Therefore, any person having ordinary skill in this field may determine an appropriate effective dosage of the peptide for treating sepsis of the present invention.

The peptide for treating sepsis of the present invention has excellent sepsis therapeutic effect, and thus may be used in the preparation of a pharmaceutical composition for treating sepsis.

Accordingly, the present invention provides a pharmaceutical composition for treating sepsis containing the peptide for treating sepsis as an active ingredient.

In addition, the present invention may provide a method for preventing or treating sepsis or septic shock including administering the pharmaceutical composition to a subject, in which the subject may be a sepsis patient, and the subject may be a subject infected or suspected of being infected with a causative organism causing sepsis.

Since the pharmaceutical composition for treating sepsis contains the previously described peptide for treating sepsis as an active ingredient, overlapping descriptions will be omitted.

As used herein, the term "treatment" refers to all of the actions by which symptoms of sepsis have taken a turn for the better or been modified favorably by administration of the peptide or the pharmaceutical composition containing the same according to the present invention.

As used herein, the term "contained as an active ingredient" refers to an amount sufficient to treat s disease at a reasonable benefit/risk ratio applicable to medical treatment. Effective dose levels may be determined by the elements including a type of a patient's disease, severity, drug activity, sensitivity to a drug, administration time, an administration route and an excretion rate, the duration of treatment and drugs used simultaneously, and the other elements well known in the field of medicine. The peptide or the pharmaceutical composition containing the same according to the present invention may be administered separately or in combination with other therapeutic agents, and may be sequentially or simultaneously administered with a conventional therapeutic agent, or administered in a single dose or multiple doses. In consideration of all of the above-mentioned elements, it is important to administer an amount that can achieve the maximum effect with the minimum amount without side effects, and such an amount may be easily determined by those skilled in the art. The dosage and frequency of administration of the pharmaceutical composition of the present invention is determined according to the type of drug as an active ingredient, along with several related factors such as the route of administration, the age, gender and weight of a patient, and the severity of a disease.

Accordingly, the pharmaceutical composition according to the present invention may include various pharmaceutically acceptable carriers as long as the peptide according to the present invention is contained as an active ingredient.

As the pharmaceutically acceptable carrier, a binder, a glydent, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, pills, capsules, sustained-release preparations, or the like.

As examples of carriers, excipients, or diluents suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a flavor, a preservative, and the like may further be included.

The present invention provides a food composition for preventing or alleviating sepsis containing the peptide for treating sepsis as an active ingredient.

Since the food composition uses the peptide for treating sepsis, overlapping content between them is omitted to avoid excessive description of the specification.

In the present invention, the food composition may be provided in a form of powder, granule, tablet, capsule, syrup, beverage, or pill, and is used together with other food or food additives in addition to the active ingredient, a peptide for treating sepsis, and may be used appropriately according to a common method. The mixing amount of the active ingredient may be properly determined according to the purpose of use, for example, prophylactic, health or therapeutic treatment.

The effective dose of the active ingredient contained in the food composition may be used in accordance with the effective dose of the pharmaceutical composition, but in the case of long-term intake for health and hygiene purposes or for health control purposes, the effective dose may be less than or equal to the above range, and it is clear that it can be used in an amount above the above range because the active ingredient has no problem in safety.

The food composition includes ingredients commonly added during food production. For example, the food composition includes a protein, a carbohydrate, a fat, a nutrient, a seasoning, and a flavoring agent. Examples of the carbohydrate include monosaccharides such as glucose and fructose; disaccharides such as maltose, sucrose, and oligosaccharides; and polysaccharides such as conventional sugars such as dextrin and cyclodextrin, and sugar alcohols such as xylitol, sorbitol, and erythritol. For the flavoring agents, natural flavoring agents and artificial flavoring agents may be used. For example, the food composition of the present invention, when prepared into a drink, may further contain citric acid, liquefied fructose, sugar, glucose, acetic acid, malic acid, or fruit juice, in addition to the active ingredient of the present invention.

The peptide containing the amino acid sequence represented by SEQ ID NO: 1 according to an example of the present invention is excellent in inhibiting the inflammatory response induced by macrophages and is excellent in inhibiting the increase in the number of bacterial colonies, and thus may be usefully used for the treatment of sepsis.

BRIEF DESCRIPTION OF THE DRAWINGS

These and/or other aspects, features, and advantages of the present invention will become apparent and more readily appreciated from the following description of example embodiments, taken in conjunction with the accompanying drawings of which:

FIG. 13A shows the structure of the cell penetrating peptide-tuftsin-rRv2626c conjugate designed in one embodiment of the present invention, FIG. 13B is a result of purifying Rv2626c-CA (active conformation) and Rv2626c-DN (TRAF6 binding capacity loss form) peptides.

FIGS. 16A, 16B, and 16C are results of identifying the change in mortality after administration of different doses of rRv2626c-CA or Rv2626c-DN peptides to mice having induced sepsis;

FIG. 20 is a result of identifying the in vivo distribution and residence time after administration of the fluorescent rRv2626c-CA peptide to mice having induced sepsis;

FIG. 23A is a result of identifying the change in the number of bacterial colonies in blood and peritoneal fluid after administration of the rRv2626c-CA peptide to mice induced to sepsis.

DETAILED DESCRIPTION

Figure 1A:
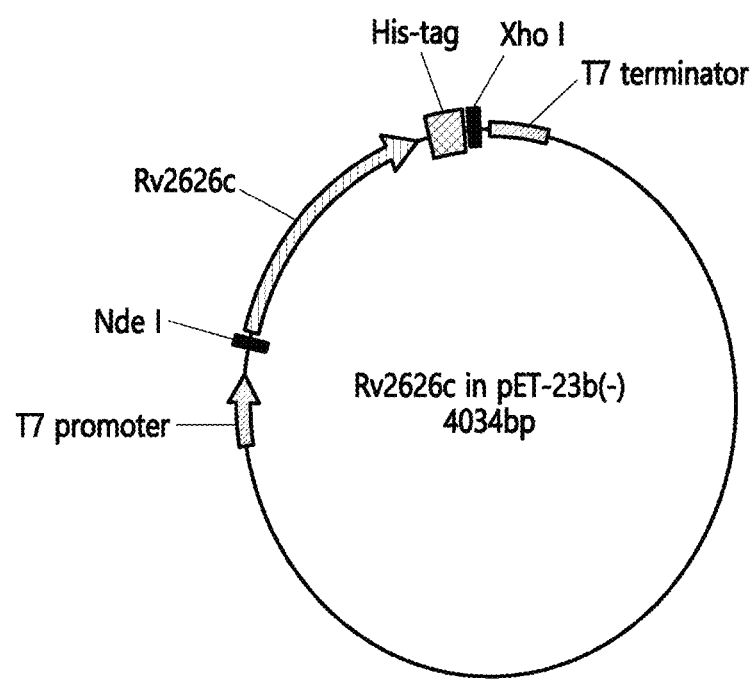
FIG. 1A is a schematic diagram of Rv2626c cloned from the pET-23b (−) vector.

Hereinafter, preferred examples of the present invention are presented to aid in the understanding of the present invention. However, the following examples are provided only to facilitate a better understanding of the present invention and the scope of the present invention is not limited to the following examples.

Experimental Methods

1. Mice and Cell Culture

Wild-type C57BL/6 mice were purchased from Samtaco Bio Korea (Gyeonggi-do, Korea). Primary bone marrow-derived macrophages (BMDMs) were isolated from C57BL/6 mice and cultured in DMEM supplemented with M-CSF (R&D Systems, 416-ML) for 3 to 5 days. BMDMs (TLR2$^{-/-}$, TLR4$^{-/-}$, MyD88$^{-/-}$, IRAK1$^{-/-}$, TRAF6$^{-/-}$, and TBK1$^{-/-}$) of C57BL/6 mice were provided by Dr. Cheol-Ho Lee (Laboratory Animal Center, Korea Research Institute of Bioscience and Biotechnology; Daejeon, Korea) and the experiment was conducted. HEK293T (ATCC-11268; American Type Culture Collection), RAW264.7 (ATCC TIB-71) and THP-1 (ATCC-TIB-202) cells were cultured in DMEM supplemented with 10% FBS (Gibco, USA), sodium pyruvate, nonessential amino acids, penicillin G (100 IU/ml), and streptomycin (100 μg/ml) or in RPMI1640 (Gibco). Transfection was performed transiently using calcium phosphate (Clonetech, USA) in 293T according to manufacturer's instructions. Stable cell lines of RAW264.7 and THP-1 were generated by transfection using standard selection methods with Lipofectamine 3000 (Invitrogen, USA) and G418 (400-800 μg/ml).

2. Recombinant Protein Construction

In order to obtain Rv2626c (GenBank accession no. NP 217142.1) and CPP-Tuftsin-Rv2626c CBS2 (aa 123-131) protein of recombinant MTB H37Rv strain, Rv2626c amino acids (1-143) and CPP sequence (GRKKRRQRRRPQ), macrophage target sequence (TKPR), and CBS2 (LPE-HAIVQF), each of the above sequences was cloned into the pRSFDuet-1 vector (Novagen) using the N-terminal 6×His tag according to the company's recommended protocol. Then, the vector was introduced into *Escherichia coli* BL21 (DE3) pLysS, and expression was induced to collect and purify the recombinant protein. Purified rRv2626c was dialyzed using a permeable cellulose membrane, and lipopolysaccharide (LPS) contamination was tested by Limulus amebocyte lysate assay (BioWhittaker). The rGRA7 protein experimented in the present invention contains less than 20 pg/ml of LPS.

3. Reagents and Antibodies

LPS (*Escherichia coli* O111:B4) and BLP (*Escherichia coli* Braun Lipoprotein) (Pam2CSK4) were purchased from Invivogen. Phospho-(Ser473)-AKT, phospho-(Thr202/Tyr204)-p42/44, phospho-(Thr180/Tyr182)-p38, phospho-(Thr183/Tyr185)-SAPK/JNK, phospho-(Ser32/36)-IκB-α, K63-Poly-Ub (D7A11), and K48-Poly-Ub (D9D5) antibodies were purchased from Cell Signaling Technology (Danvers, MA, USA). IκB-α (C-21), TRAF6 (H-274), Lamin B1 (B-10), Tubulin (5F131), CD68 (KP1), F4/80 (BM8), CD3 (PC3/188A), CD19 (5J25-C1), Ub (P4D1), His (His17), HA (12CA5), Flag (D-8), GST (B-14), Myc (9E10), and Actin (I-19) antibodies were purchased from Santa Cruz Biotechnology.

4. Plasmid Design

HA-tagged ubiquitin (Ub), K48-related (linkage) specific ubiquitin (K48-Ub), and K63-related specific ubiquitin (K63-Ub) plasmids were purchased from Addgene. Plasmids containing all of TRAF6 and modified plasmids have been described in the related art (*Infect Immun* 84: 339-50). Plasmids encoding different regions of Rv2626c (1-143, 8-65, and 73-131, see Table 1) were amplified from the full-length Rv2626c cDNA by PCR amplification, and were generated by sub-cloning into a pEBG derivative encoding an N-terminal GST epitope tag between BamHI and NotI. All plasmids were derived from the pEBG-GST mammalian fusion vector and the pEF-IRES-Puro expression vector for excessive and stable expression in mammalian cells. All plasmid sequences were analyzed with the ABI PRISM 377 automatic DNA sequencer to identify whether they were 100% identical to the original sequences. FIG. 1A shows a schematic diagram of Rv2626c cloned from the pET-23b (−) vector.

5. Peptides

Tat-linked Rv2626c peptides were synthesized by Peptron (Korea) and purified in the form of an acetate salt to avoid abnormal reactions in cells. The amino acid sequence of each peptide is shown in Table 1. The LPS concentration measured by Limulus amebocyte lysate assay (BioWhittaker) is contained in the peptide used in the experiment as less than 3-5 pg/ml.

TABLE 1

| Names | Sequences (From N to C) |
|---|---|
| Tat | RRRQRRKKRGY |
| Tat-Rv2626c-(73-131) | RRRQRRKKRGY-G-LARDSIYYVDA NASIQEMLNVMEEHQVRRVPVISEH RLVGIVTEADIARHLPEHAIVQF |
| Tat-Rv2626c-(73-82) | RRRQRRKKRGY-G-LARDSIYYVD |
| Tat-Rv2626c-(83-92) | RRRQRRKKRGY-G-ANASIQEMLN |
| Tat-Rv2626c-(93-102) | RRRQRRKKRGY-G-VMEEHQVRRV |
| Tat-Rv2626c-(103-112) | RRRQRRKKRGY-G-PVISEHRLVG |
| Tat-Rv2626c-(113-122) | RRRQRRKKRGY-G-IVTEADIARH |
| Tat-Rv2626c-(123-131) | RRRQRRKKRGY-G-LPEHAIVQF |
| Tat-Rv2626c-(E125K) | RRRQRRKKRGY-G-LPKHAIVQF |
| Tat-Rv2626c-(E125Q) | RRRQRRKKRGY-G-LPQHAIVQF |

TABLE 1-continued

| Names | Sequences (From N to C) |
|---|---|
| Tat-Rv2626c-(H126D) | RRRQRRKKRGY-G-LPEDAIVQF |
| Tat-Rv2626c-(H126Q) | RRRQRRKKRGY-G-LPEQAIVQF |

6. GST Pulldown, Immunoblot and Immunoprecipitation Experiments

Cells were collected, and cells were lysed with NP-40 buffer (50 mM HEPES, pH 7.4, 150 mM NaCl, 1 mM EDTA) supplemented with a protease inhibitor (Roche) at a concentration of 1% (v/v). After centrifugation, the supernatant was reacted with protein A/G beads at 4° C. for 2 hours. The pretreated lysate was mixed with a 50% suspension of glutathione-binding sepharose beads (Amersham Biosciences) and reacted at 4° C. for 4 hours. After the reaction was completed, the precipitate was washed extensively with a lysis buffer. Proteins bound to glutathione beads were boiled for 5 minutes and eluted with SDS loading buffer.

For immunoprecipitation, cells were collected and lysed with NP-40 buffer to which a protease inhibitor was added. Cell lysate and protein A/G agarose beads were reacted at 4° C. for 1 hour to pre-clear the unnecessary reaction. Thereafter, 1-4 μg of antibody was added to 1 ml of the cell lysate, reacted at 4° C. for 8 to 12 hours, and protein A/G agarose beads were treated for 6 hours. The immunoprecipitates were then washed with lysis buffer, boiled for 5 minutes, and eluted with SDS loading buffer.

For immunoblotting, the polypeptide was denatured by SDS-polyacrylamide gel electrophoresis (PAGE) and transferred to a PVDF membrane (Bio-Rad). After the PVDF membrane was reacted with a specific antibody, antibody binding was visualized by chemiluminescence (ECL; Millipore), and the signal was detected with a Vilber chemiluminescence analyzer (Fusion SL 3; Vilber Lourmat).

7. Protein Purification and Mass Spectrometry

In order to identify the protein binding to rRv2626c, THP-1 cells were lysed with NP-40 buffer to which a protease inhibitor was added after treatment with or without rRv2626c for 30 minutes. After centrifugation, the supernatant was reacted with protein A/G beads at 40° C. for 2 hours to perform pre-clearing. The pre-cleared cell lysate was mixed with α-His antibody conjugated with agarose beads at 4° C. for 4 hours. Thereafter, the precipitates were washed with a lysis buffer, and the protein bound to the beads was eluted and then separated from a Nupage 4-12% Bis-Tris gradient gel (Invitrogen). After silver staining (Invitrogen), specific protein bands were extracted by ion-trap mass spectrometry, and amino acid sequences were determined by tandem mass spectrometry and database search.

8. Quantitative Real-Time Polymerase Chain Reaction (RT-PCR)

Total RNA was extracted from cells with RNeasy RNA extraction mini-kit (Qiagen). cDNA was synthesized with the Enzynomix kit (Enzynomix), and quantitative PCR was performed with a gene-specific primer set (Bioneer) and SYBR green PCR master mix (Roche). Real-time PCR was performed using QuantStudio™ 3 (ABI) according to manufacturer's instructions. Data were normalized to expression of β-actin. The relative expression level was calculated using the delta-delta Ct method. The sequences of the primers are shown in Table 2.

TABLE 2

| Genes | | Sequences |
|---|---|---|
| mCD86 | Forward | gcacgtctaagcaaggtcac |
| | Reverse | catatgccacacaccatccg |
| miNOS | Forward | ccccgctactactccatcag |
| | Reverse | ccactgacacttcgcacaaa |
| mCD163 | Forward | tgtgaccatgctgaggatgt |
| | Reverse | ctcgaccaatggcactgatg |
| mArg1 | Forward | ctgagctttgatgtcgacgg |
| | Reverse | tcctctgctgtcttcccaag |
| mβ-Actin | Forward | aagtgtgacgttgacatc |
| | Reverse | gatccacatctgctggaagg |

9. Confocal Fluorescence Microscopy

Immunofluorescence analysis was performed by confocal fluorescence microscopy. Cells were fixed on coverslips with 4% (w/v) paraformaldehyde dissolved in PBS, and cells were permeabilized with PBS containing 0.25% (v/v) Triton X-100 at 25° C. for 10 minutes. TRAF6 or His was detected by reacting with the primary antibody diluted in 1/100 at 25° C. for 1 hour. After washing, TRAF6 or His was reacted with a fluorescently labeled secondary antibody at 25° C. for 1 hour. Slides were checked with a laser scanning confocal microscope (model LSM 800; Zeiss).

10. Cell Sorting

The cytosol and mitochondria were separated using the mitochondria fractionation kit (Active Motif, 40015). The intracellular fractionated protein was dissolved in a buffer containing 2% SDS, boiled with 2x reducing sample buffer, and then used for SDS-PAGE.

11. MTT Assay

After culturing the cells of each experimental group for a specified time, 5 mg/ml of MTT (3-(4,5-dimethylthiazol-2-yl)-2,5-diphenyltetrazolium bromide) solution was added to the medium and cultured for an additional 4 hours. After removing all the media, the same volume of DMSO (dimethyl sulfoxide) solution was added to dissolve formazan for 15 minutes. Cell viability was identified by measuring the absorbance at 540 nm with a UV/VIS spectrophotometer.

12. Flow Cytometry

Flow cytometry data were collected at FACSCanto (BD Biosciences, San Diego, CA) and analyzed with FlowJo software (Tree Star, Ashland, OR). In order to identify the expression of cell surface proteins, cells and mAb were reacted at 4° C. for 20 to 30 minutes, and the cells were fixed with Cytofix/Cytoperm solution (BD Biosciences). The mAb clones used were as follows: NK1.1 (PK136, eBioscience), LY6G (1A8-Ly6g, eBioscience), SR-A (PSL204, eBioscience), FcR (MAR-1, eBioscience), TLR2 (6C2, eBioscience), TLR4 (HTA125, eBioscience), NRP1 (3DS304M, eBioscience) and CXCR2 (eBio5E8-C7-F10, 5E8-C7-F10, eBioscience).

13. ELISA (Enzyme-Linked Immunosorbent Assay)

The levels of TNF-α, IL-6, IL-1β, IL-12p40 and IL-10 were identified in cell culture supernatants and mouse serum with the BD OptEIA ELISA set (BD Pharmingen) according to the manufacturer's recommended procedure.

14. Sepsis Induction and Checking Number of Bacteria

Cecal ligation and puncture (CLP) was performed on 6-week-old C57BL/6 female mice (Samtaco Bio). Specifically, mice were anesthetized with pentothal sodium (50 mg/kg, i.p.) and a small abdominal midline incision was made to expose the cecum. The cecum was then connected under the ileocecal valve, the surface was punctured twice with a 22-gauge needle, and the abdomen was sutured. The survival rate of mice was checked every day for 7 days, and all animals were bred in a pathogen-free environment.

The number of bacteria was checked as follows. Blood and peritoneal lavage fluid were collected from mice through cardiac foramen at defined times after CLP, and blood was serially diluted. Then, 5 µl of each diluted solution was plated into a blood agar plate, and the bacteria were cultured at 37° C. for 24 hours. The number of bacteria was calculated by counting colony forming units per total peritoneal lavage fluid or blood.

15. Tissue Analysis

For tissue analysis, the spleen, liver and lungs of mice were fixed in 10% formalin and placed in paraffin. Paraffin sections (4 µm) were cut and stained with hematoxylin and eosin (H&E). Histopathological scores (0 to 4) were scored independently for each organ section by a pathologist based on the severity of inflammation and the number and distribution of inflammatory cells in the tissue without prior knowledge of the treatment group.

16. In Vivo Imaging rRv2626c-CA/Cy5.5 was prepared by adding streptavidin-binding Cy5.5 dye to rRv2626c-CA, and rRv2626c-CA/Cy5.5 was administered to CLP mice by intraperitoneal injection (i.p). In order to study tissue biodistribution, mice were sacrificed at different time zones after administration, and major organs were imaged with an IVIS spectrum-CT in vivo imaging system (PerkinElmer, Inc.).

17. Statistical Analysis

All data were analyzed using Student's t-test with Bonferroni adjustment or ANOVA for multiple comparisons and described as mean±SD. Statistical analysis was performed with the SPSS (version 12.0) statistical software program (SPSS, Chicago, IL, USA). Differences were considered significant at $p<0.05$. For survival, data were graphed and analyzed by the product restriction method of Kaplan and Meier using the log-rank (Mantele-Cox) test for comparison using GraphPad prism (version 5.0, La Jolla, CA, USA).

Experiment Results

1. In Macrophages, rRv2626c Regulates the Inflammatory Response Through the TLR Signaling Pathway.

Figure 1B:
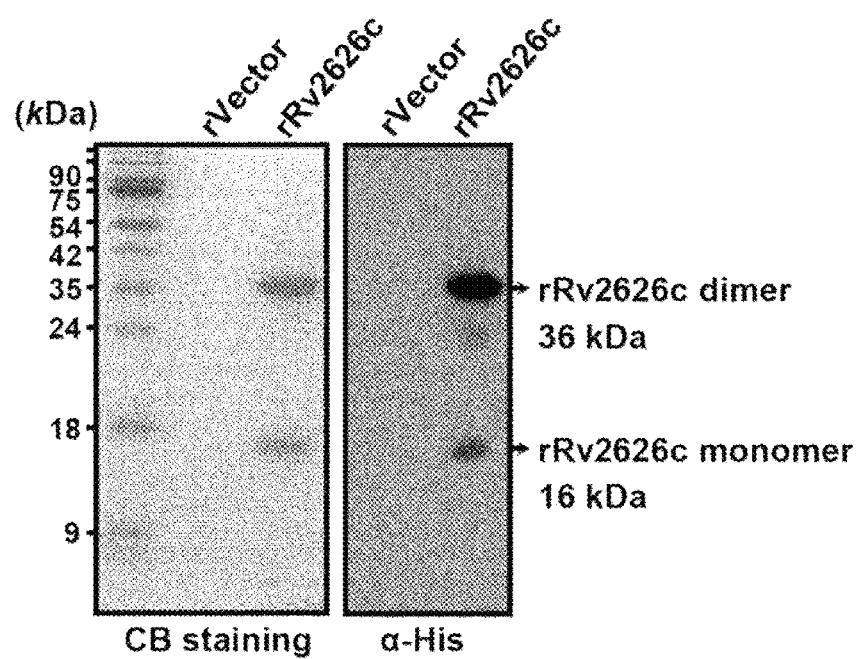
FIG. 1B is a result of identifying the rRv2626c peptide (16 and 36 kDa) derived from the purified *Mycobacterium tuberculosis* by SDS-PAGE and immunoblotting.
Figure 1C:
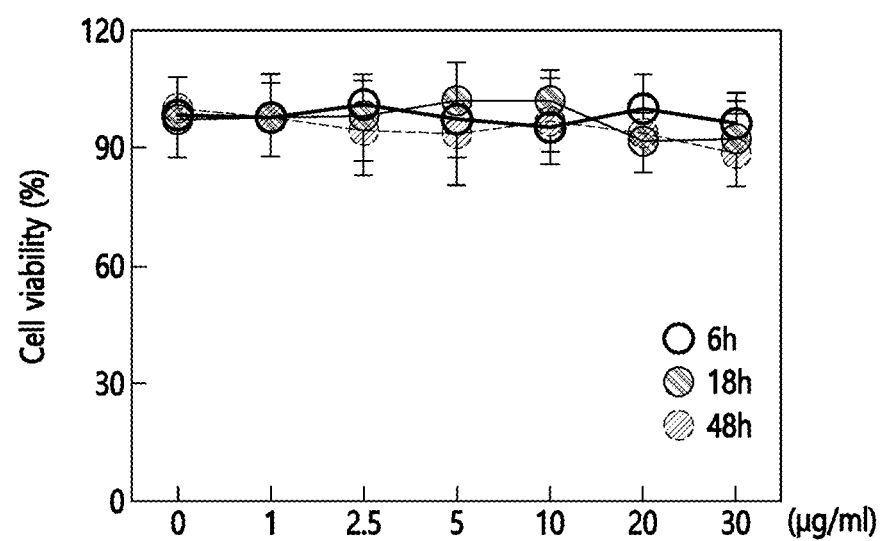
FIG. 1C is a result of measuring the level of cytotoxicity after treatment of macrophages with the rRv2626c peptide.
Figure 2A:
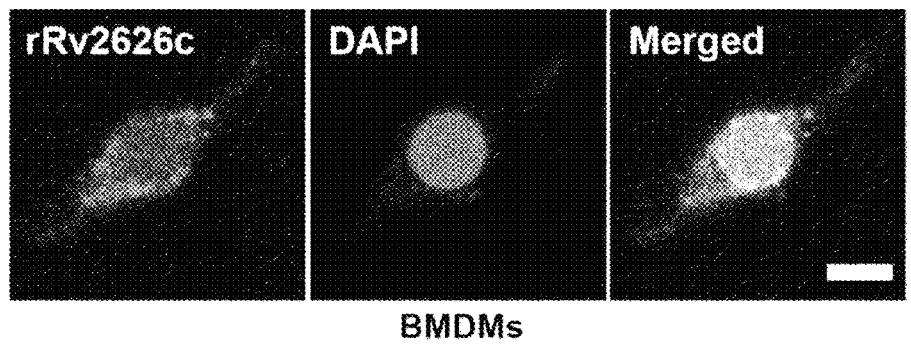
FIG. 2A is a result of identifying the intracellular distribution location of rRv2626c by confocal microscopy after treatment of macrophages with the rRv2626c peptide.
Figure 2B:
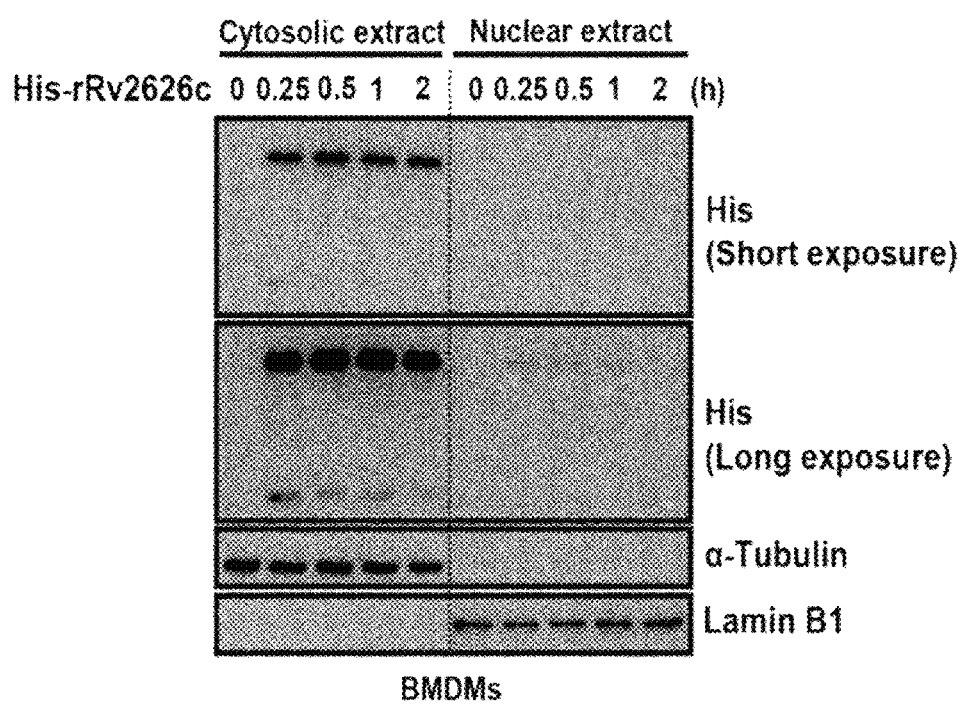
FIG. 2B is a result of identifying the intracellular fraction analysis after treatment of macrophages with the rRv2626c peptide.

In order to test the role of Rv2626c in the early immune response of macrophages, His-tagged rRv2626c was constructed. Purified rRv2626c (16, 36 kDa) was identified by SDS-PAGE and immunoblotting (FIG. 1B). The cytotoxicity induced by rRv2626c in macrophages did not show a significant difference (FIG. 1C). In addition, it was identified that rRv2626c was distributed in the cytoplasm of macrophages through the results of confocal microscopic analysis and cell fraction analysis (FIGS. 2A and 2B).

In a previous study, the present inventors identified that rRv2626c was attached to the cell surface and located in macrophages to regulate NF-κB and promote cytokine production. Accordingly, in order to examine the functional effect of rRv2626c in macrophages, the production amount of cytokine induced by rRv2626c was identified by ELISA.

Figure 3A:
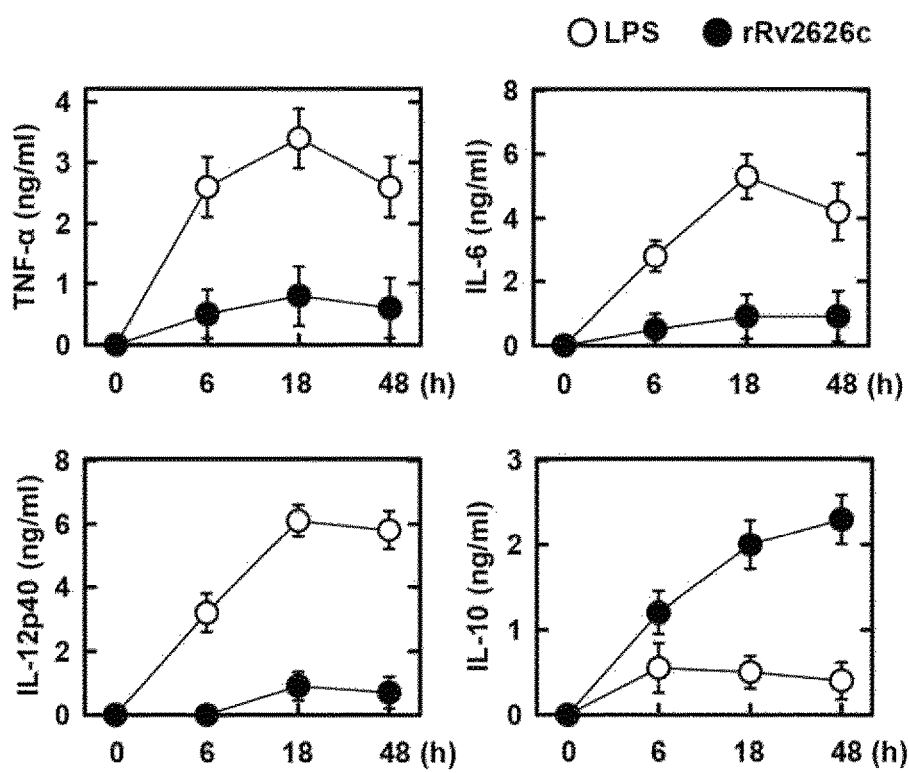
FIG. 3A is a result of identifying the cytokine production level after treatment of macrophages with the rRv2626c peptide.
Figure 3B:
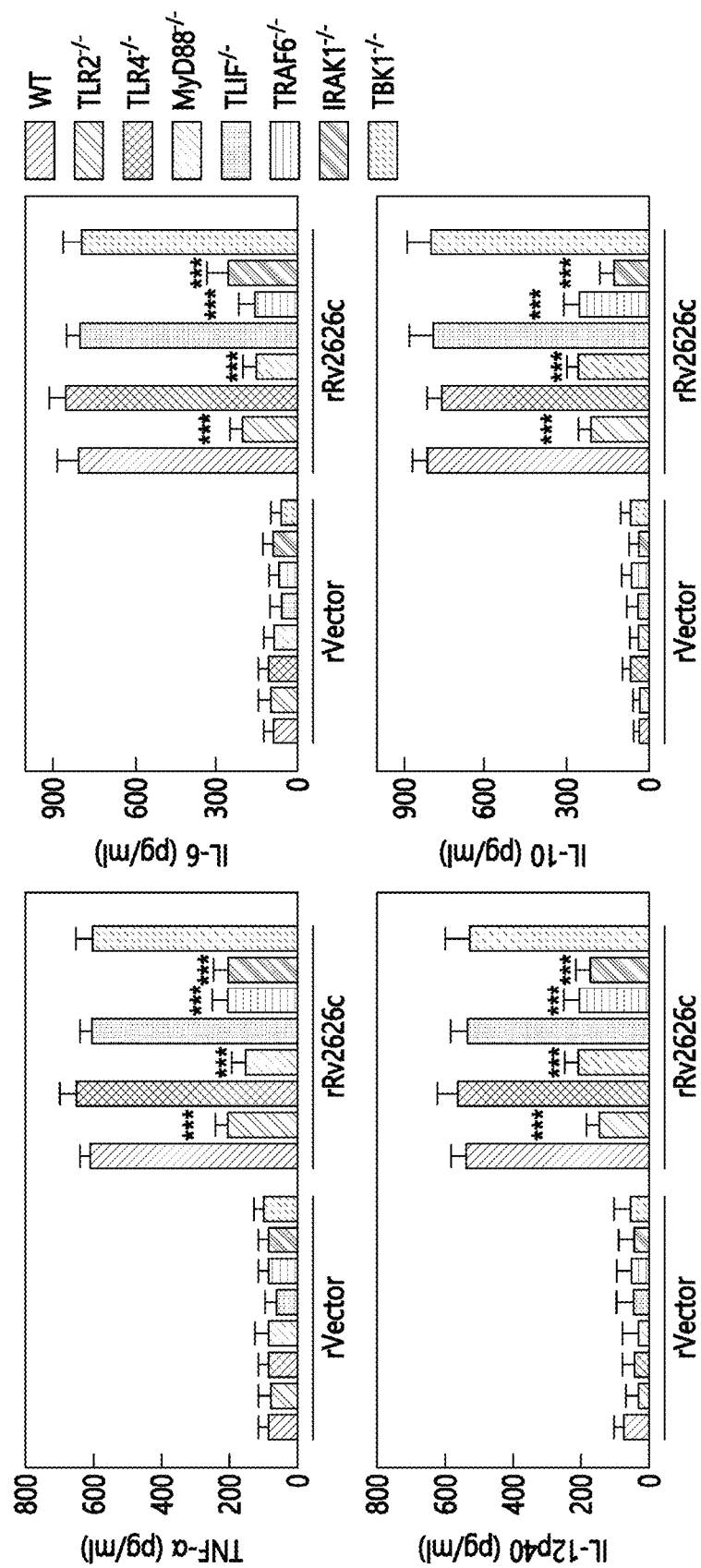
FIG. 3B is a result of identifying the cytokine production level after treatment of TLR2$^{-/-}$, TLR4$^{-/-}$, MyD88$^{-/-}$, IRAK1$^{-/-}$, TRAF6$^{-/-}$, or TBK1$^{-/-}$ macrophages with the rRv2626c peptide.
Figure 3C:
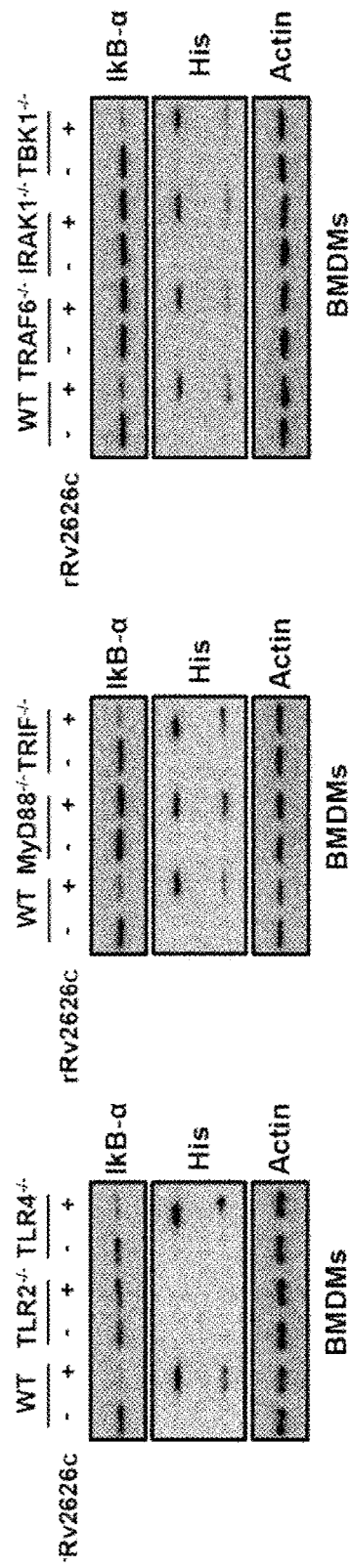
FIG. 3C is a result of identifying endocytosis after treatment of TLR2$^{-/-}$ or TLR4$^{-/-}$ macrophages with the rRv2626c peptide.

As a result of identification, rRv2626c decreased the production of pro-inflammatory cytokines (TNF-α, IL-6 and IL-12p40) and increased the production of anti-inflammatory cytokines (IL-10) (FIGS. 3A and 3B). Those results were dependent on the TLR2-MyD88-TRAF6-IRAK1 pathway, not the TRIF-dependent (TBK1) pathway. In addition, rRv2626c was internalized into macrophages, and His-tagged rRv2626c was not detected only in cell lysates of rRv2626c-treated TLR2$^{-/-}$ BMDMs (FIG. 3C). These results suggest that rRv2626c is internalized into macrophages via TLR2, and that a TLR2-MyD88-dependent pathway is important in the inflammatory response mediated by rRv2626c.

2. rRv2626c Inhibits TLR-Mediated Inflammatory Response in Macrophages.

Figure 4A:
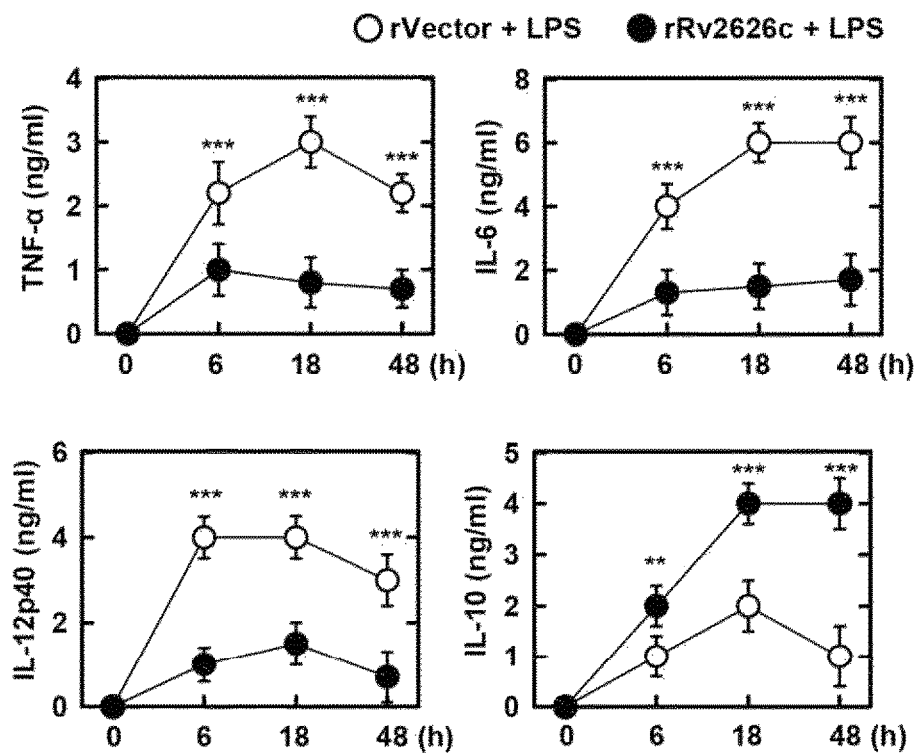
FIG. 4A is a result of identifying the production level of inflammatory cytokines by treating macrophages with lipopolysaccharide (LPS) to induce an inflammatory response and then treating the macrophages with the rRv2626c peptide.
Figure 4B:
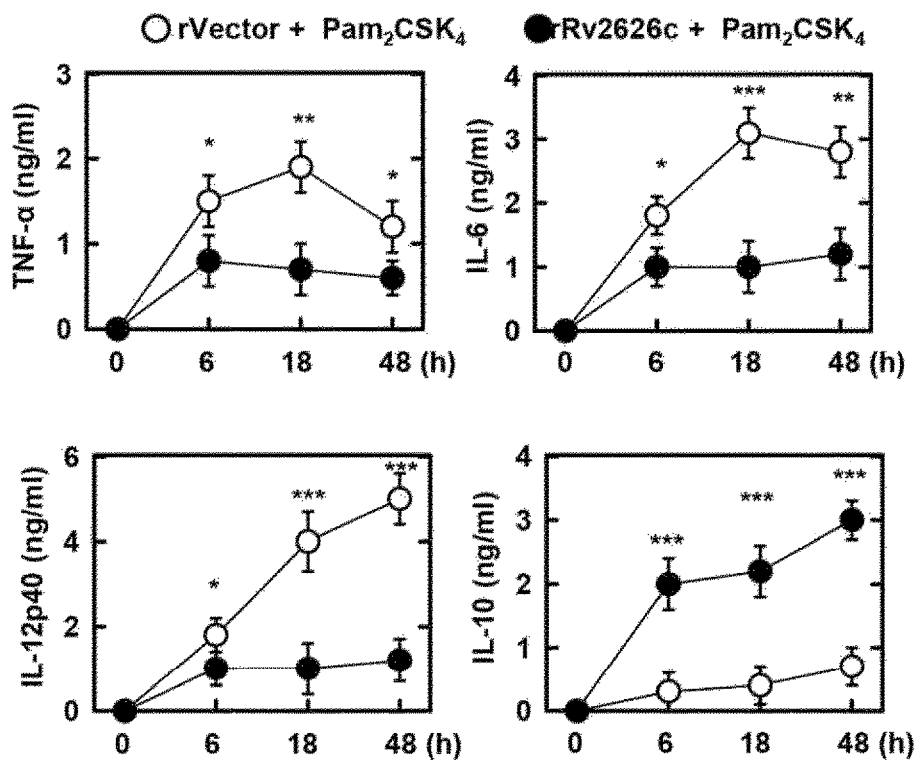
FIG. 4B is a result of identifying the production level of inflammatory cytokines by treating macrophages with Pam$_2$CSK$_4$ to induce an inflammatory response and then treating the macrophages with the rRv2626c peptide.

In order to identify the functional role of Rv2626c in the TLR-mediated inflammatory signaling pathway, it was investigated whether Rv2626c inhibited the production of inflammatory cytokines induced by TLR4 (LPS) or TLR2/6 (Pam$_2$CSK$_4$). As a result of identification, rRv2626c attenuated the production of TLR-mediated pro-inflammatory cytokines (TNF-α, IL-6 and IL-12p40) and, conversely, promoted the production of anti-inflammatory cytokines (IL-10) (FIG. 4). Based on the above results, the present inventors hypothesized that rRv2626c would enter macrophages via TLR2 and that intracellular rRv2626c would perform any function to regulate signaling pathways induced by TLR ligands.

Figure 5:
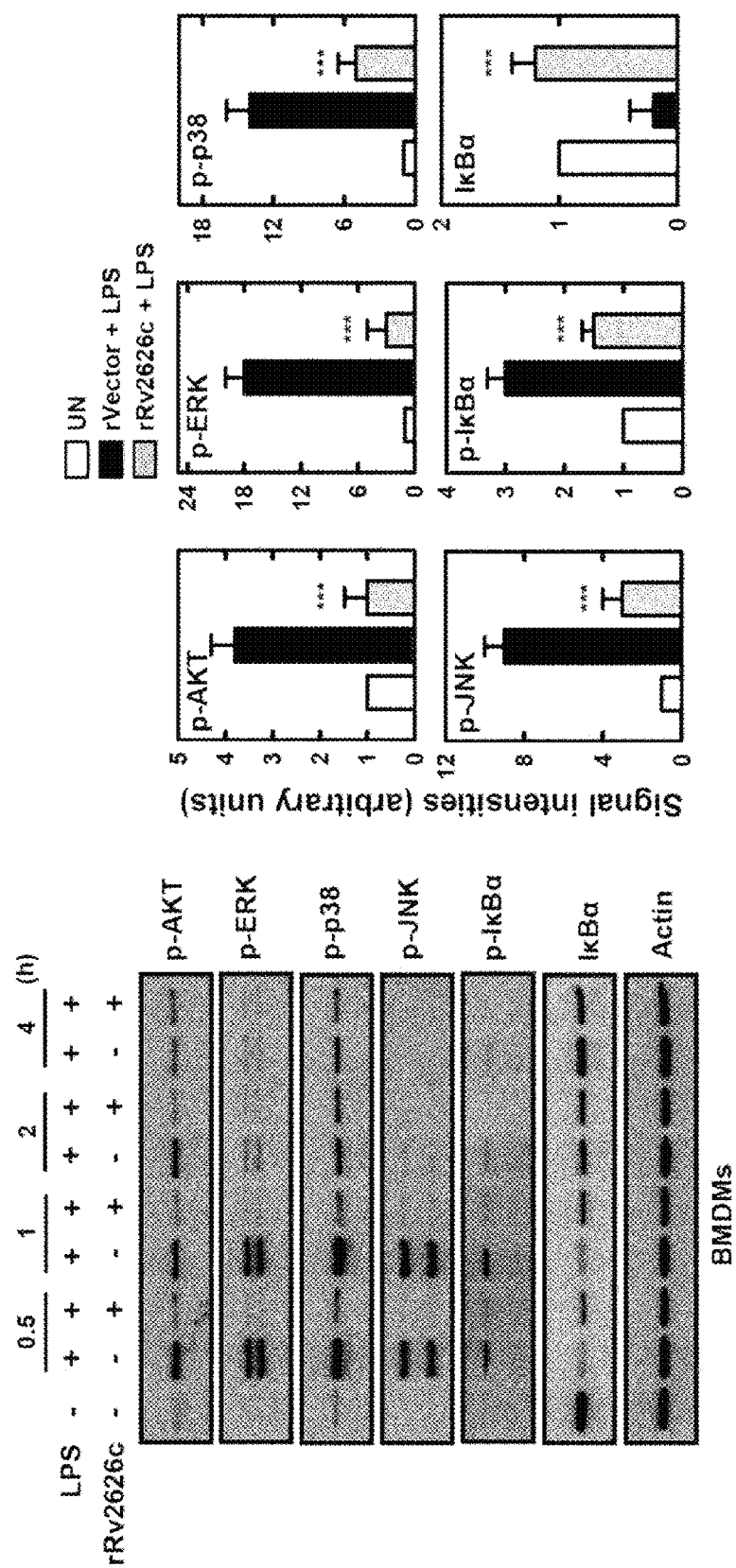
FIG. 5 is a result of identifying the activation of signal molecules involved in the inflammatory response of macrophages by treating LPS-treated macrophages with the rRv2626c peptide.

Since the PI3K, MAPK, and NF-κB signaling pathways are presently known to be involved in inflammatory signals of LPS-induced macrophages, it was investigated whether the activation of signaling proteins in these pathways is affected by rRv2626c. As a result, it was identified that LPS-induced phosphorylation of AKT, MAPK and IκBα and degradation of IκBα were inhibited by pretreatment with rRv2626c (FIG. 5). Taken together, these results suggest that rRv2626c acts as a modulator to inhibit TLR ligand-induced activation in PI3K, MAPK, and NF-κB signaling pathways, thereby inhibiting pro-inflammatory cytokine production and promoting anti-inflammatory cytokine production in macrophages.

3. Rv2626c Interacts with TRAF6.

The present inventors hypothesized that rRv2626c would modulate the LPS-induced TLR signaling pathway through binding to innate immune signaling molecules. In order to identify the binding partner of rRv2626c, THP-1 cells were treated with His-tagged rVector or rRv2626c, cultured, and co-immunoprecipitated with His-agarose beads.

Figure 6:
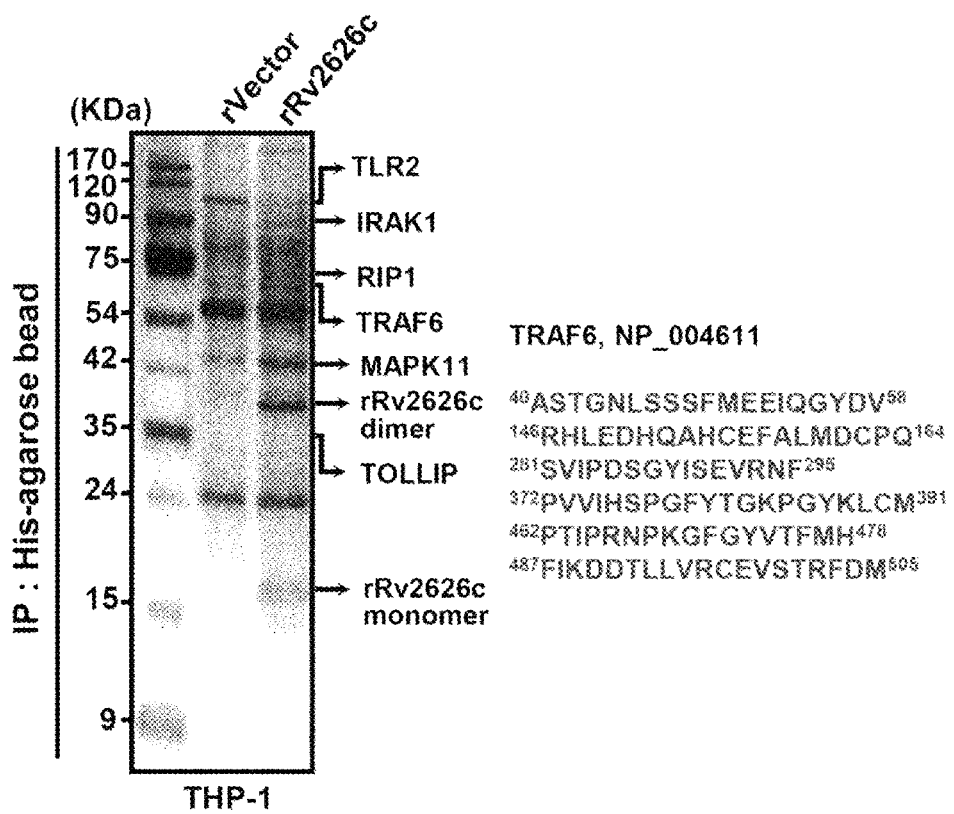
FIG. 6 is a result of identifying the intracellular binding partner of the rRv2626c peptide.
Figure 7A:
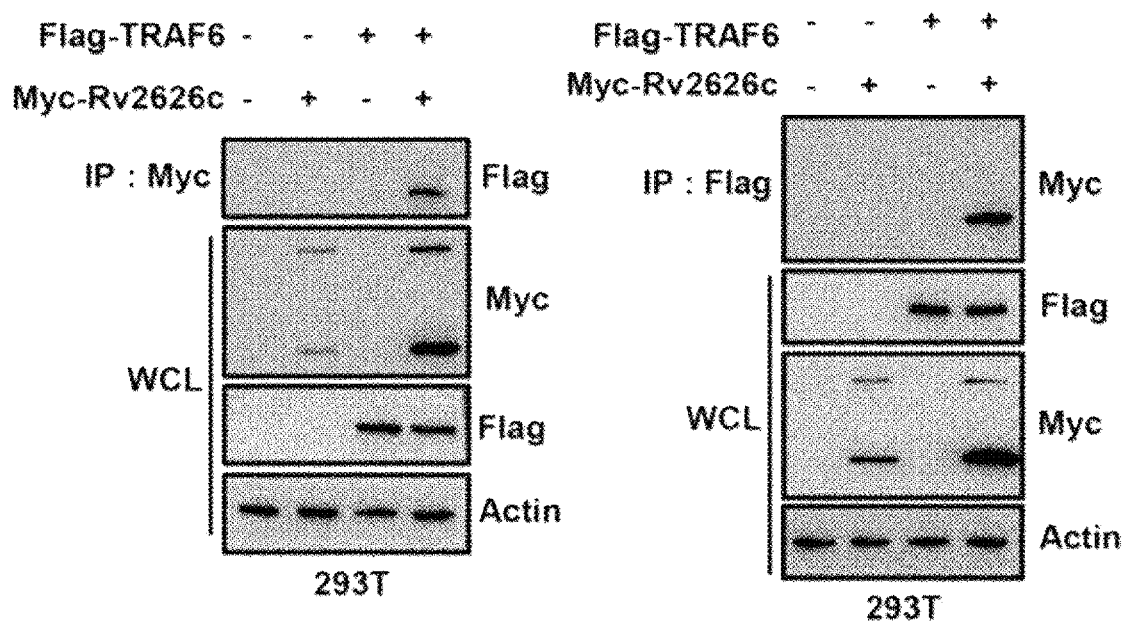
FIG. 7A is a result of identifying the binding of the rRv2626c peptide to TRAF6 by immunoprecipitation in HEK 293T cells.
Figure 7B:
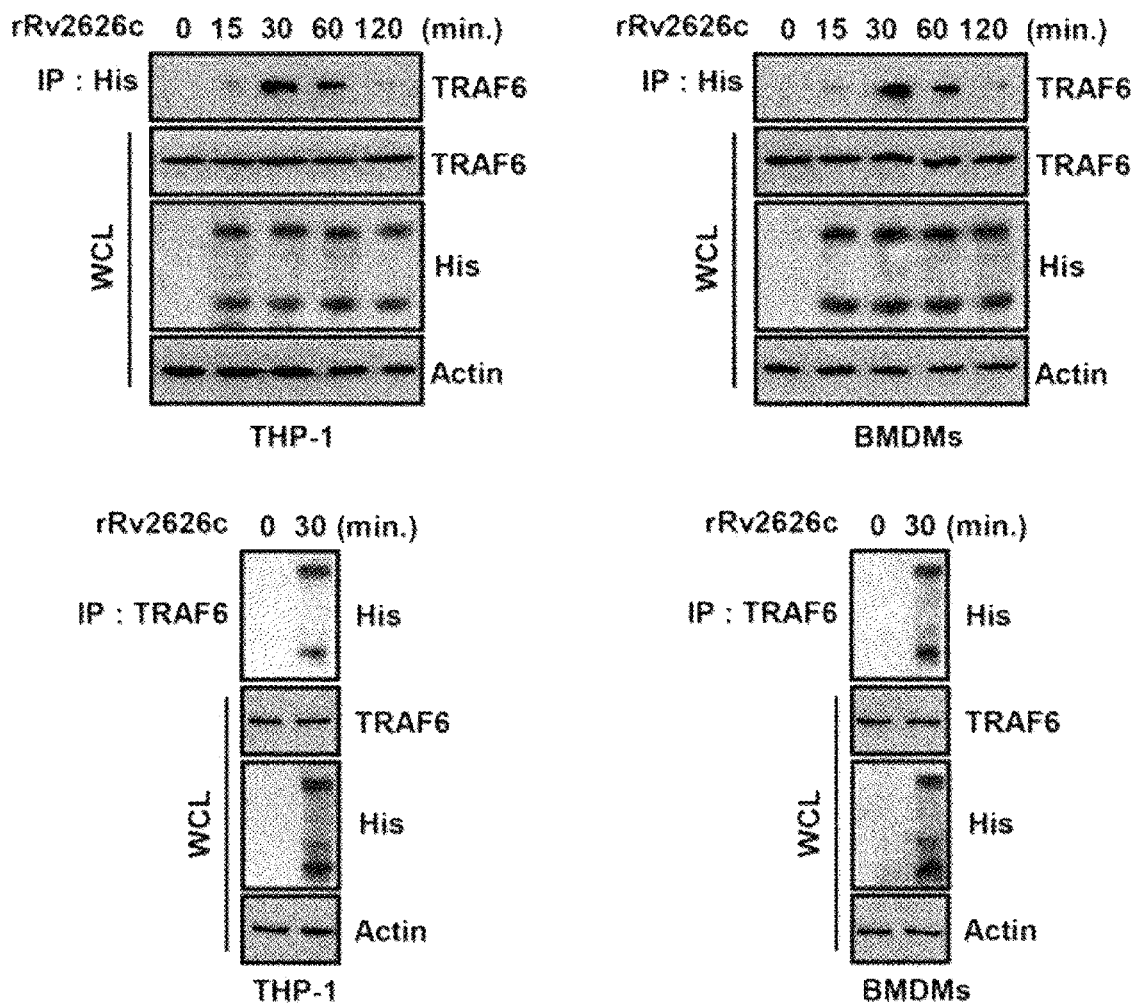
FIG. 7B is a result of identifying the binding of the rRv2626c peptide to TRAF6 by immunoprecipitation in THP-1 cells.
Figure 8:
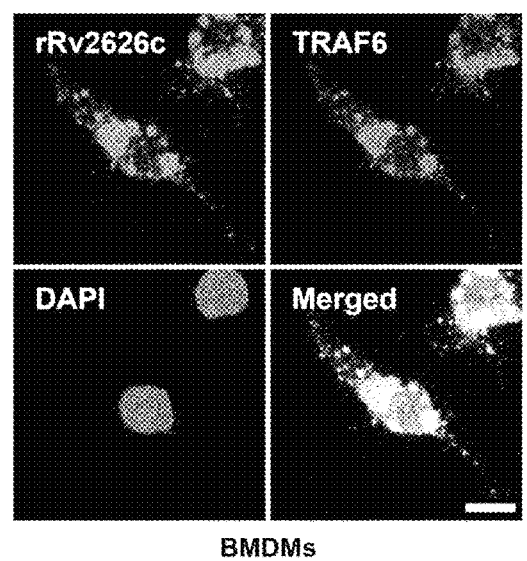
FIG. 8 is a result of identifying the intracellular localization of the rRv2626c peptide and TRAF6 in macrophages.

As a result of mass spectrometry, several endogenous proteins predicted to bind rRv2626c, including TLR2 (100 kDa), IRAK1 (80 kDa), RIP1 (70 kDa), TRAF6 (60 kDa), MAPK11 (41 kDa) and TOLLIP (32 kDa) were identified (FIG. 6). Immunoprecipitation results in 293T cells (ectopic expression of TRAF6) and macrophages showed that rRv2626c interacted strongly with TRAF6, although transiently (30 minutes to 60 minutes) (FIG. 7). In addition, according to confocal microscopy images of rRv2626c and TRAF6, rRv2626c was mainly co-located with endogenous TRAF6 in the cytoplasm of macrophages (FIG. 8). These results suggest that rRv2626c directly interacts with TRAF6, a signaling molecule of the TLR signaling pathway, at both endogenous and ectopic levels.

4. The CBS2 Domain of Rv2626c Interacts with the N-Terminal Region of TRAF6 and Attenuates Poly-Ubiquitination of TRAF6.

Figure 9A:
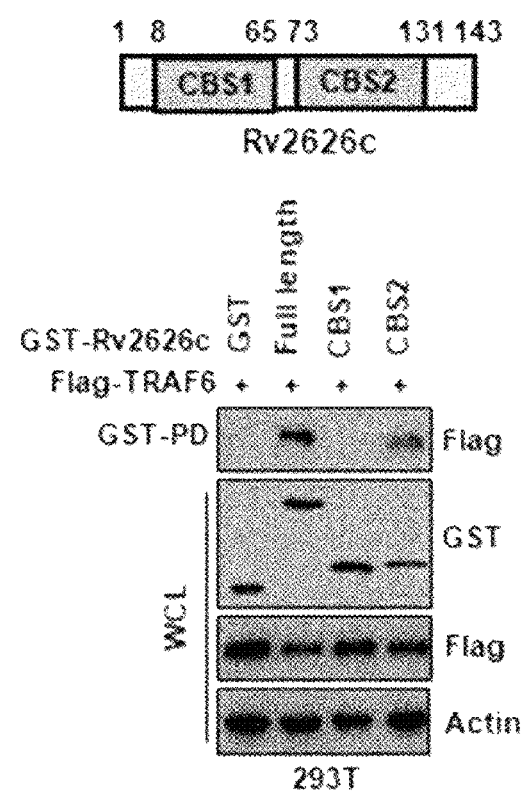
FIG. 9A is a result of identifying the domain of the rRv2626c peptide interacting with TRAF6.

As a result of identifying which domain of Rv2626c interacts with TRAF6 in HEK 293T cells, it was identified that the CBS2 domain of Rv2626c and TRAF6 bound (FIG. 9A).

In addition, the 9 to 10 amino acids sequences unit of the CBS2 domain was designed to find the detailed region of Rv2626c that mediates interaction with TRAF6, and in order to prevent proteolysis, a plurality of Tat-CBS2 peptides was prepared by adding the retro-inverso peptide HIV-1 Tat sequence to the 9 to 10 amino acids sequences of Rv2626c (Table 1). With this peptide, the minimum residue of Rv2626c that interacts with TRAF6 in 293T cells was identified.

Figure 9B:
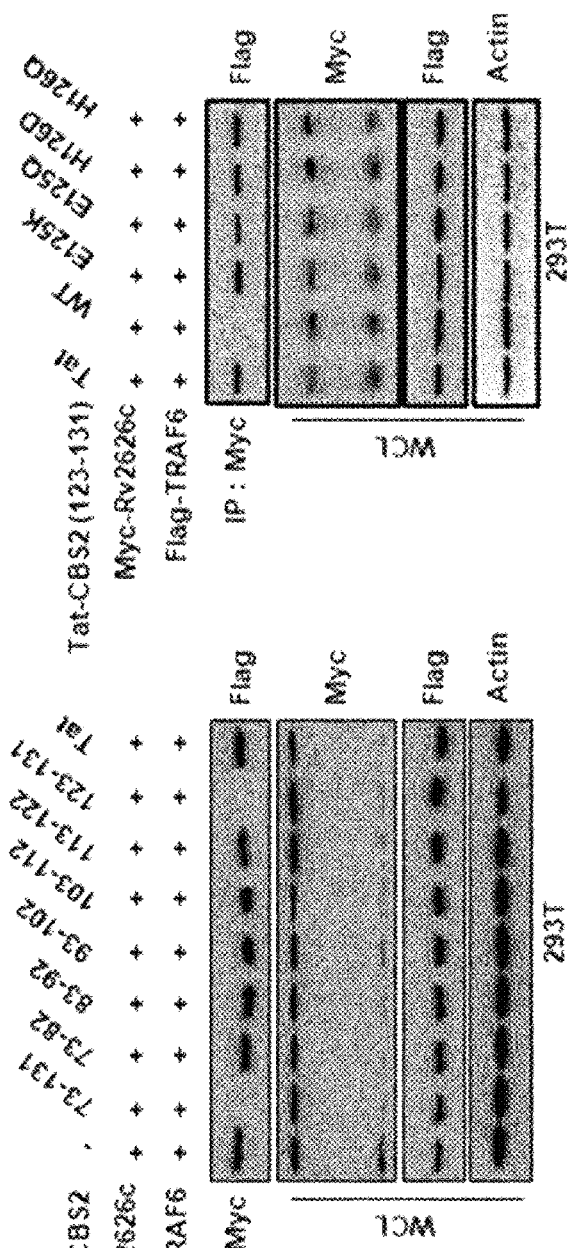
FIG. 9B is a result of identifying the amino acid sequence essential for interaction with TRAF6 in the CBS2 domain of the rRv2626c peptide.
Figure 10A:
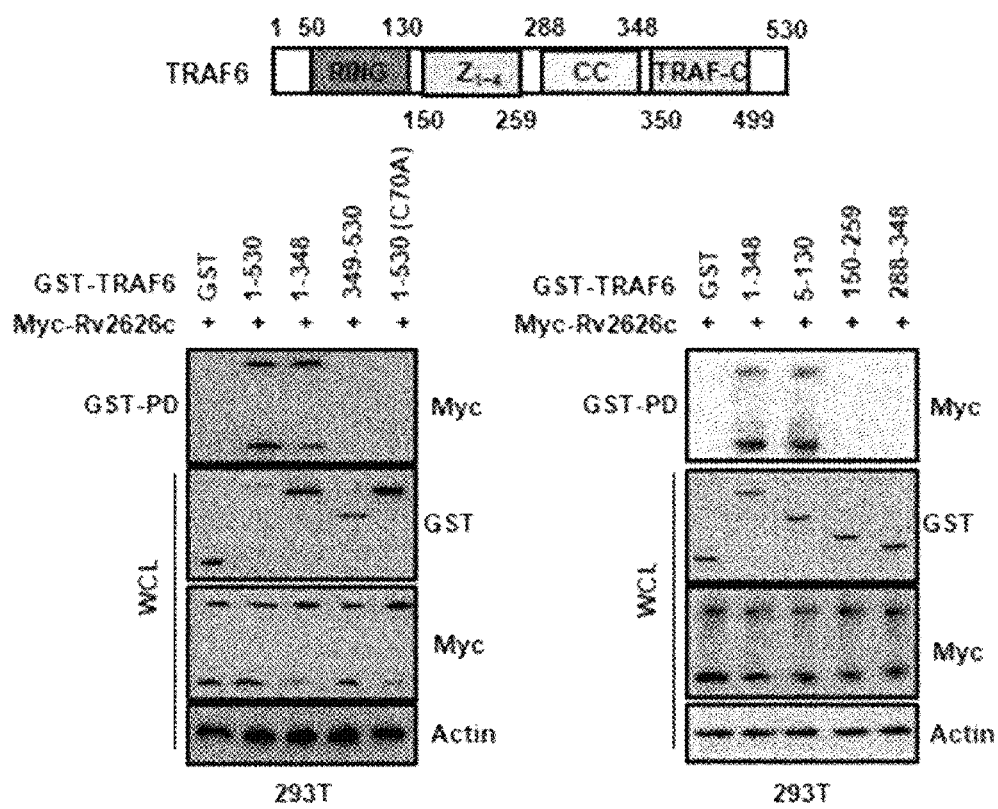
FIG. 10A is a result of identifying the domain of TRAF6 involved in the interaction with rRv2626c, and FIG. 10B schematically shows the interaction between rRv2626c and TRAF6.
Figure 10B:
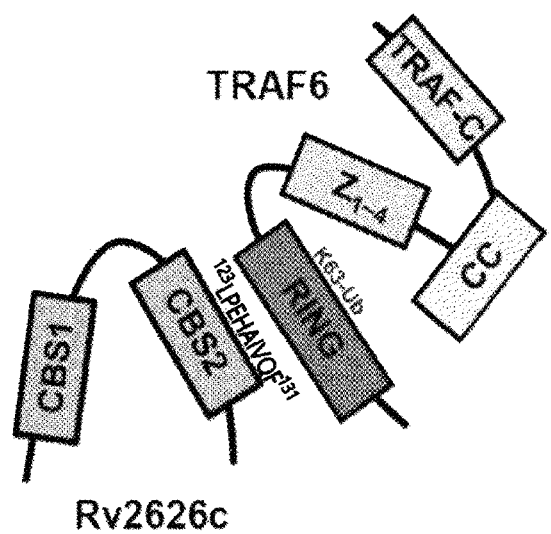

As a result of the experiment, it was found that the Tat-CBS2 (123LPEHAIVQF131) peptide effectively blocked the TRAF6 and Rv2626c interaction, whereas the Tat peptide itself could not be blocked (FIG. 9B). In particular, 125EH126 amino acids with electrically charged side chains at 9 amino acids (123LPEHAIVQF131) of CBS2 were essential for interaction with TRAF6 and were important for minimal interaction. In addition, it was identified that the RING domain of TRAF6 is required for interaction with Rv2626c through detailed mapping of various truncation mutations of Rv2626c with TRAF6 (FIG. 10A). Taken together, these results suggest that Rv2626c is directly associated with the TRAF6 N-terminal RING domain via the CBS2 domain (aa 123-131), particularly a subregion of the CBS2 domain (FIG. 10B).

Since poly-ubiquitination of TRAF6 is important for activation of TRAF6 and downstream signaling pathways, it was investigated whether the interaction between Rv2626c and TRAF6 regulates the ubiquitination status of TRAF6.

Figure 11A:
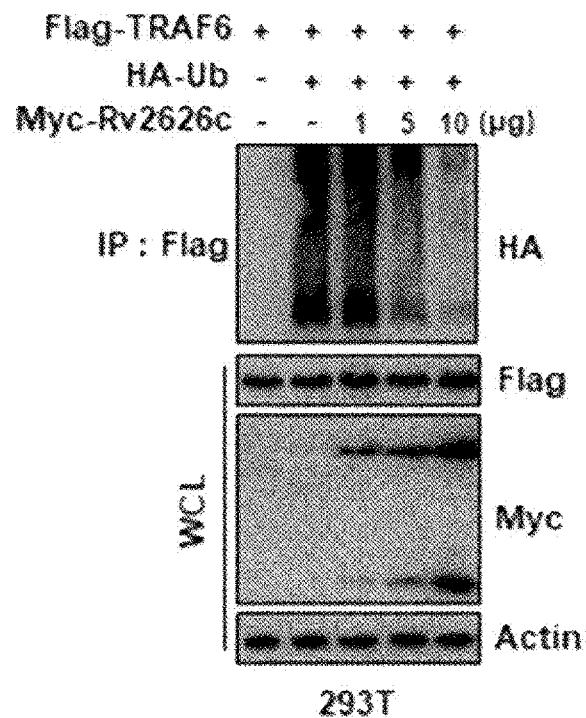
FIG. 11A is a result of identifying the change in the ubiquitination state of TRAF6 by rRv2626c with HA-ubiquitin (HA-Ub)

As a result of western blotting, it was identified that expression of HA-ubiquitin (HA-Ub) caused poly-ubiquitination of Flag-TRAF6, and that ubiquitination of TRAF6 was attenuated by Rv2626c expression in a treatment concentration-dependent manner (FIG. 11A).

It is known that K48-linked ubiquitination mediates proteasome degradation of ubiquitin substrates, whereas K63-linked ubiquitination is essential for activation of NF-κβ and downstream signaling pathways. Immunoprecipitation was performed using HA-tagged lysine48-linked ubiquitin (K48-Ub) and K63-linked ubiquitin (K63-Ub) plasmids to determine the type of ubiquitin chain regulated by Rv2626c.

Figure 11B:
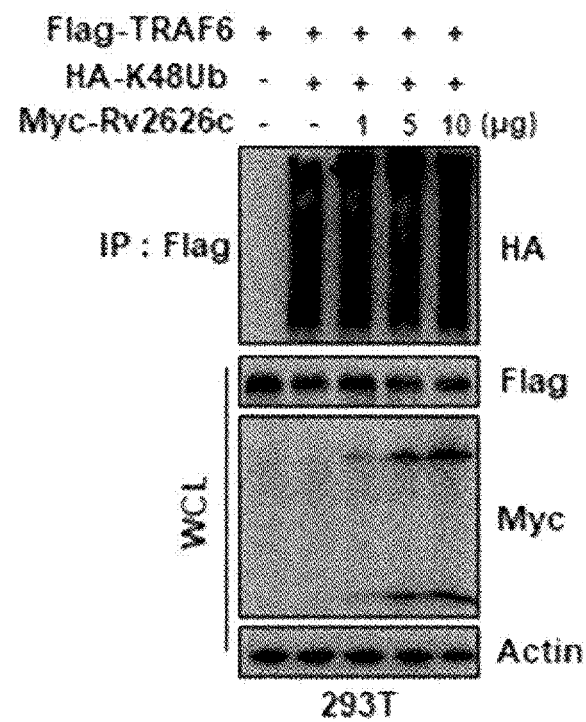
FIG. 11B is a result of identifying the change in the ubiquitination state of TRAF6 by rRv2626c with lysine(K)48-linked ubiquitin (K48-Ub)
Figure 11C:
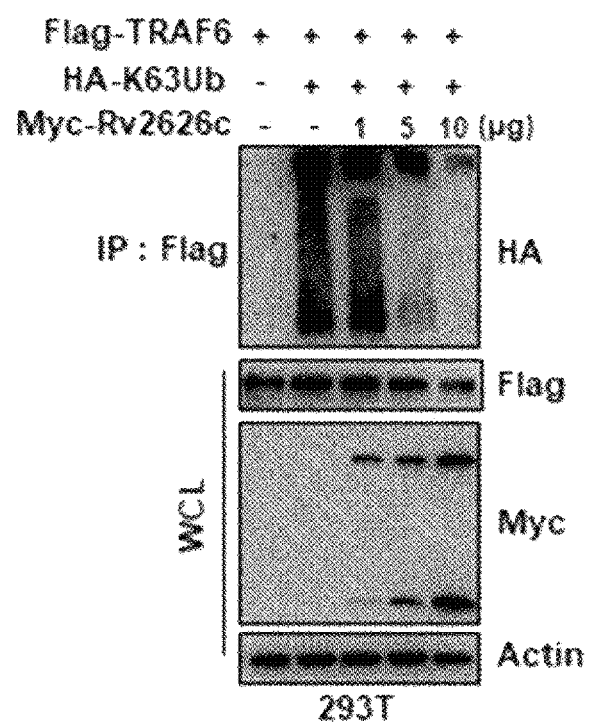
FIG. 11C is a result of identifying the change in the ubiquitination state of TRAF6 by rRv2626c with K63-linked ubiquitin (K63-Ub)
Figure 12A:
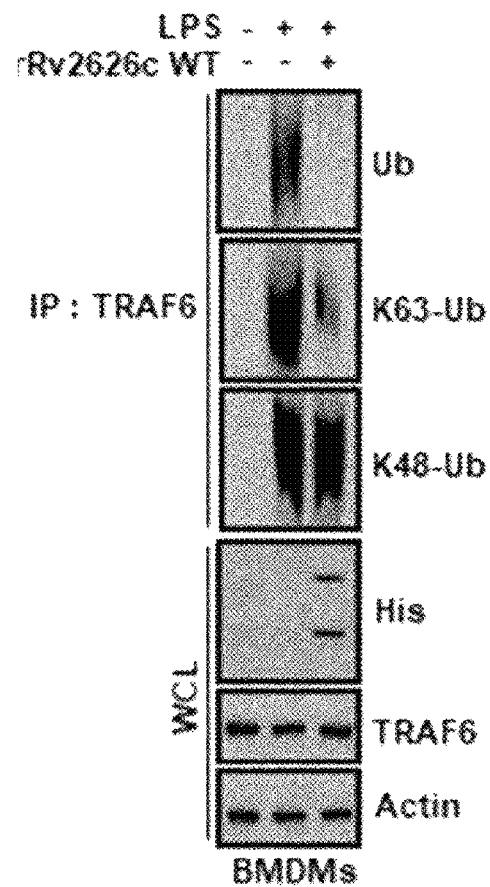
FIG. 12A is a result of identifying the change in the ubiquitination state of TRAF6 by rRv2626c with K48-Ub and K63-Ub.
Figure 12B:
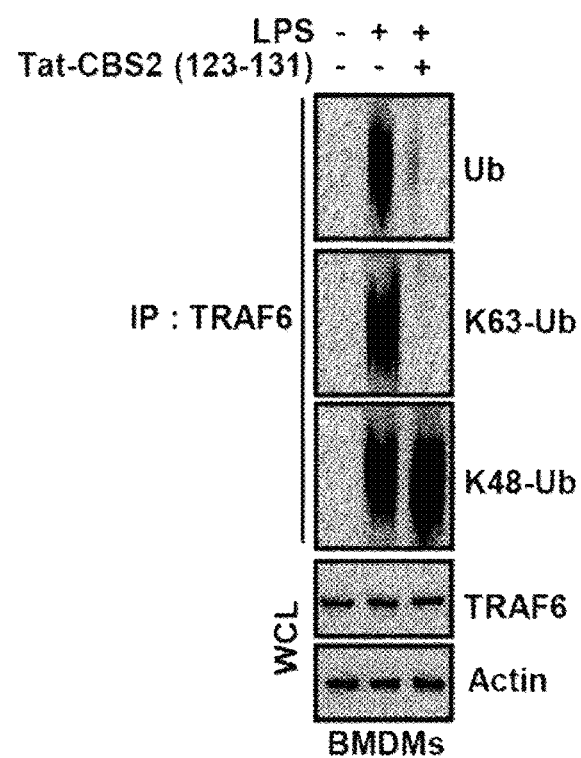
FIG. 12B is a result of identifying the change in the ubiquitination state of TRAF6 by Tat-CBS2 (123-131) with K48-Ub and K63-Ub.

As a result, it was identified that overexpression of K48-Ub and K63-Ub induced ubiquitination in TRAF6 through ubiquitin binding, respectively (FIGS. 11B and 11C). In addition, although the treatment concentration of Rv2626c increased, the K48-Ub chain had no significant effect, but the K63-Ub chain was strongly inhibited in a manner dependent on the treatment concentration of Rv2626c (FIG. 12). These results suggest that Rv2626c and TRAF6 bind, and Rv2626c inhibits poly-ubiquitination of K63-Ub of TRAF6, which regulates activation of TRAF6 and downstream signaling pathways.

5. The Tuftsin-Linked Rv2626c Peptide was Designed to Target Macrophages.

Tuftsin, four natural immunomodulatory peptides (Thr-Lys-Pro-Arg) derived from amino acid residues 289-292, a proteolytic product of IgG in the spleen, is known as phagocytosis-stimulating factors. Accordingly, the present inventors designed a cell penetrating peptide/tuftsin-conjugated Rv2626c peptide containing amino acids 123-131 of Rv2626c for macrophage targeting and immune response regulation (FIG. 13A).

Figure 13C:
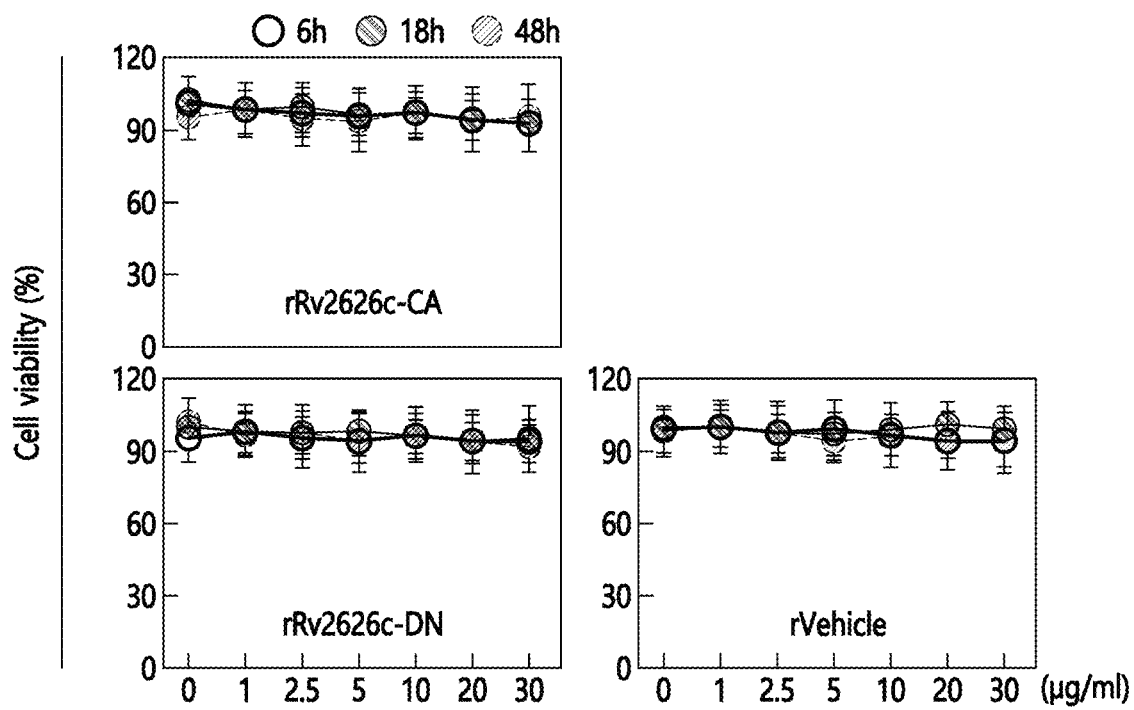
FIG. 13C is a result of identifying the cytotoxicity of the Rv2626c-CA and Rv2626c-DN peptides.

In order to evaluate the function of peptides Rv2626c-CA (active conformation) and Rv2626c-DN (TRAF6 binding capacity loss form, including E125Q and H126Q mutations) peptides in macrophages, His-tagged rRv2626c-CA and Rv2626c-DN were produced in bacteria and purified by affinity chromatography. Purified rRv2626c-CA and Rv2626c-DN were approximately 10 kDa in size and were identified by SDS-PAGE and immunoblotting (FIG. 13B). As a result of MTT analysis, no significant difference in cytotoxicity was observed between rRv2626c-CA and Rv2626c-DN in BMDM as compared to the control group (rVehicle) (FIG. 13C).

Figure 14:
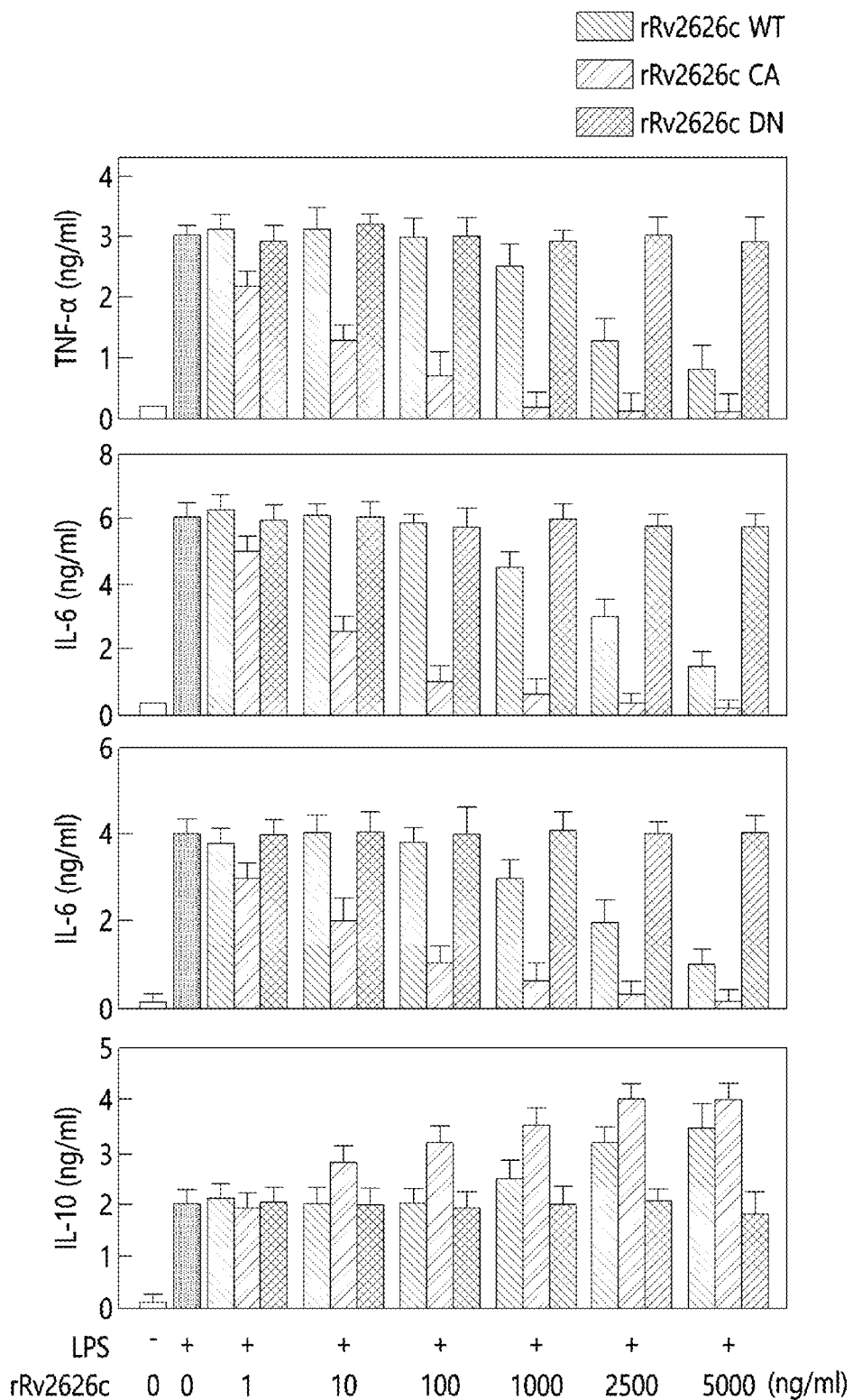
FIG. 14 is a result of identifying the production level of inflammatory cytokines by treating macrophages inducing inflammatory responses by treatment with LPS with the Rv2626c-CA or Rv2626c-DN peptide.
Figure 15:
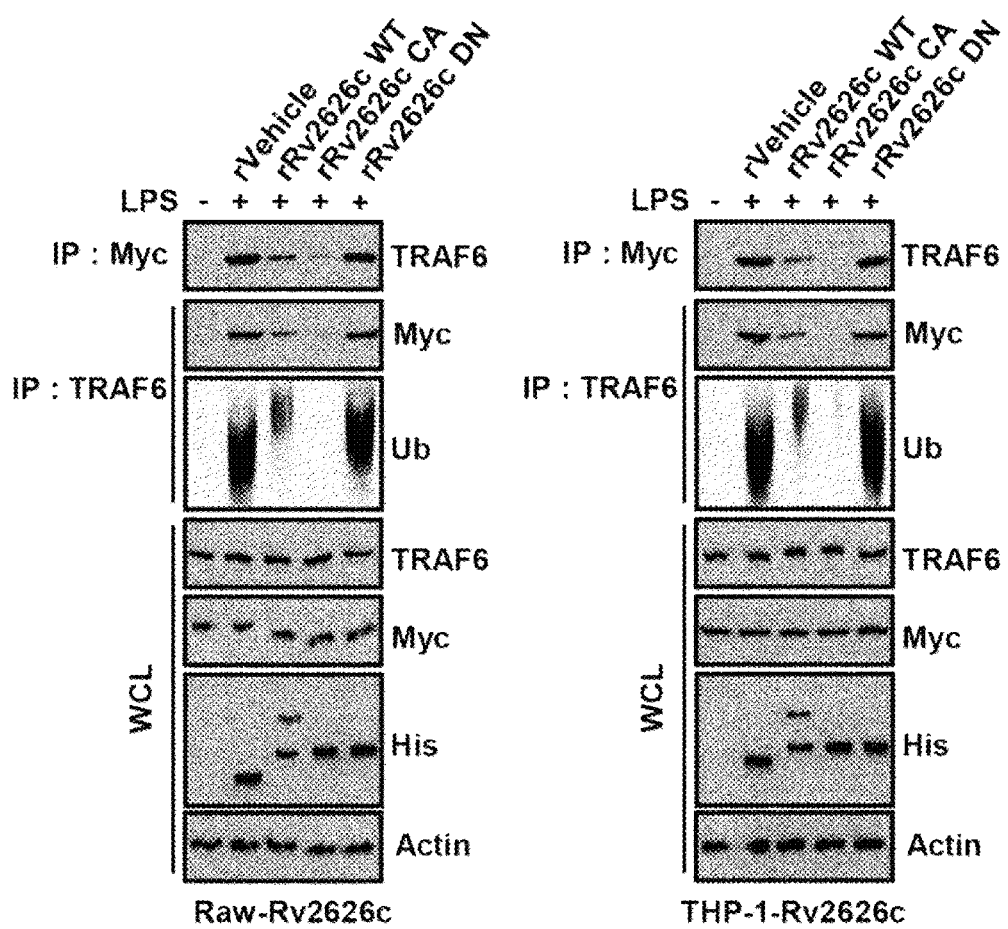
FIG. 15 is a result of identifying the binding to TRAF6 and the ubiquitination status of TRAF6 after treating LPS-treated macrophages with the Rv2626c-CA or Rv2626c-DN peptide.

In addition, it was identified whether rRv2626c-CA could mimic the pharmacological and biological profile of rRv2626c. As a result of identification, consistent with the activity of rRv2626c alone, rRv2626c-CA also modulated the inflammatory response in macrophages in a treatment concentration-dependent manner. Surprisingly, rRv2626c-CA exhibited an $IC_{50}$ value of 10 ng/ml, a 250-fold increase compared to the $IC_{50}$ of rRv2626c-WT of 2.5 μg/ml (FIG. 14). In addition, treatment with rRv2626c-CA dramatically inhibited the LPS-induced interaction between endogenous TRAF6 and Rv2626c and polyubiquitination of TRAF6 in Rv2626c-expressing cells (FIG. 15). In particular, no significant difference was observed in the inflammatory response, TRAF6 binding and polyubiquitination in the experimental group treated with rRv2626c-DN (TRAF6 binding loss) to macrophages or control group (rVehicle; tuftsin treatment) (FIGS. 14 and 15). Accordingly, rRv2626c-CA serves as a selective and potent inflammatory modulator for macrophage-targeted immune responses.

6. rRv2626c-CA Protects Mice from Systemic Sepsis.

The present inventors investigated whether rRv2626c-CA protected mice from sepsis induced by several microorganisms.

Figure 16A:
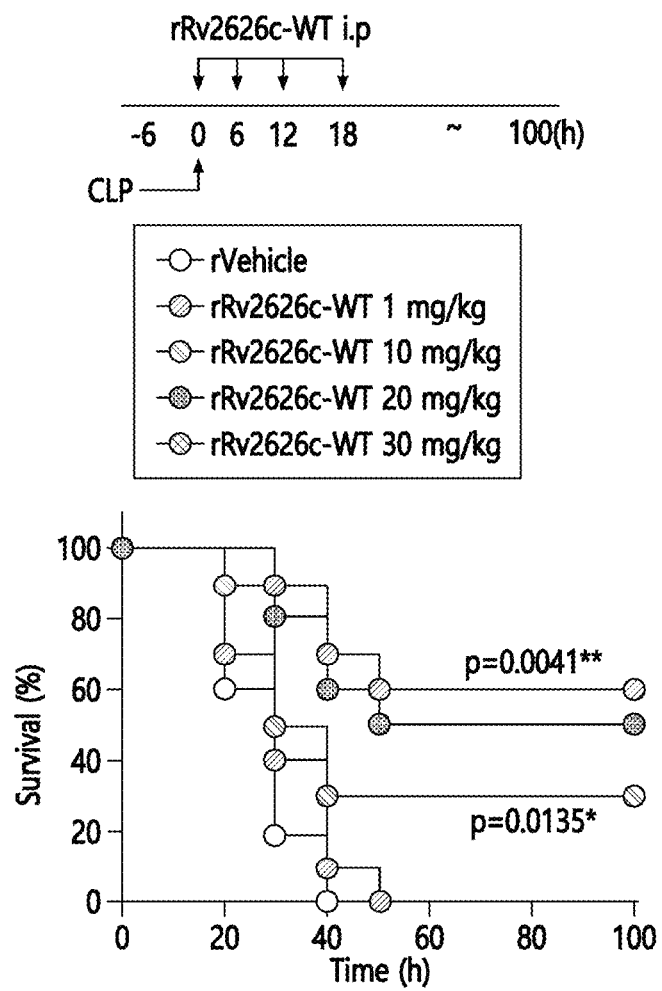
Figure 16B:
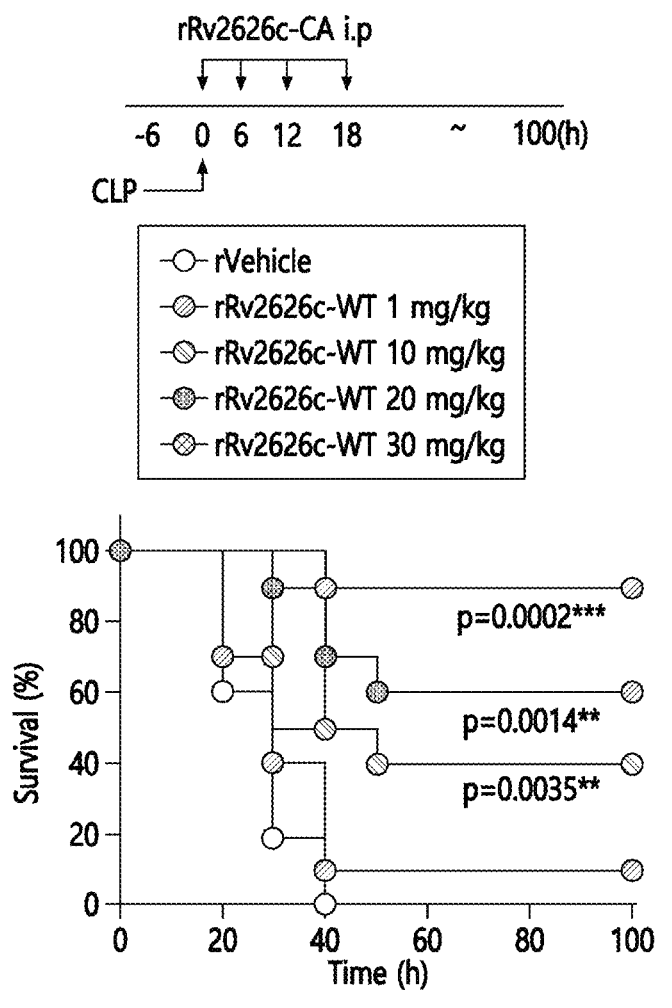
Figure 16C:
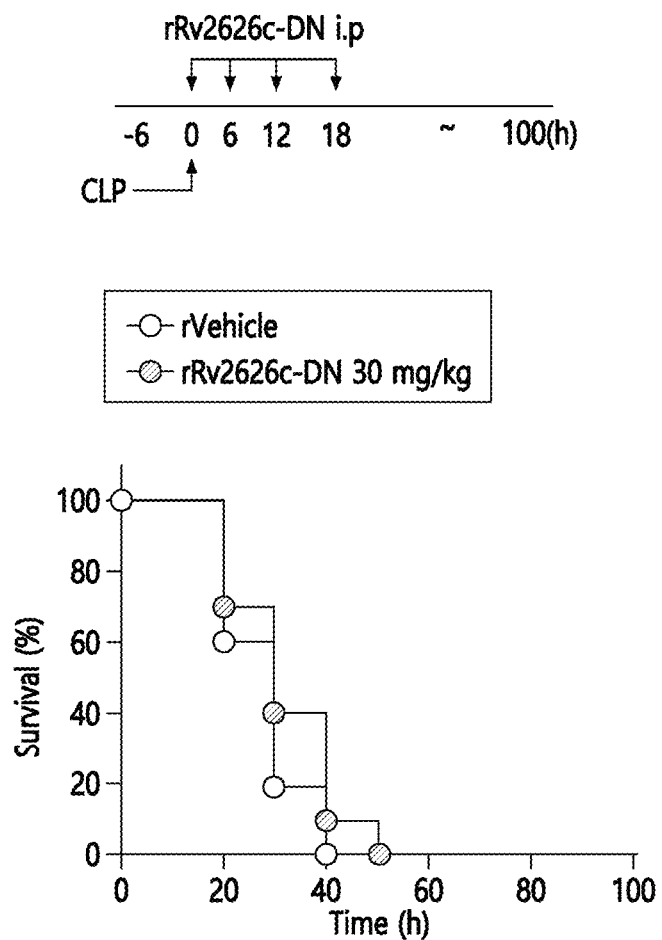

First, the efficacy of rRv2626c-CA on CLP-induced mortality in mice was tested. When CLP mice were treated with rRv2626c-CA, 4 times, through intraperitoneal injection after 0, 6, 12 and 18 hours, the mortality was reduced in a dose-dependent manner. In particular, when rRv2626c-CA was administered to mice at a dose of 100 μg/kg, 90% of mice did not die. Surprisingly, rRv2626c-CA had an $IC_{50}$ value of 20 μg/kg, which is 1000 times higher than the $IC_{50}$ value of rRv2626c-WT (CPP+rRv2626c full length) (FIGS. 16A and 16B). No significant difference was observed in the survival graph in the rRv2626c-DN (TRAF6 binding loss) administration group or the control group (rVehicle; tuftsin treatment) (FIG. 16C).

Figure 17:
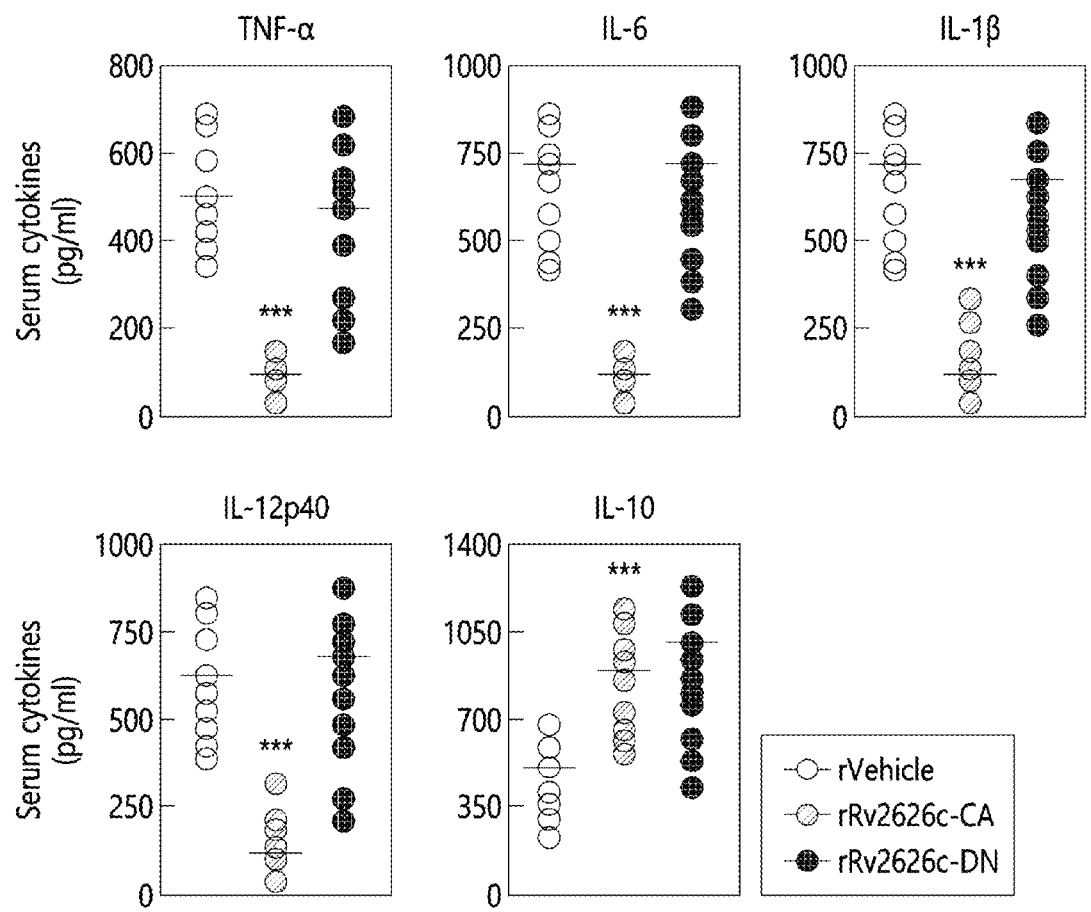
FIG. 17 is a result of identifying the level of cytokines in the serum after administration of different doses of rRv2626c-CA or Rv2626c-DN peptides to mice having induced sepsis.
Figure 18:
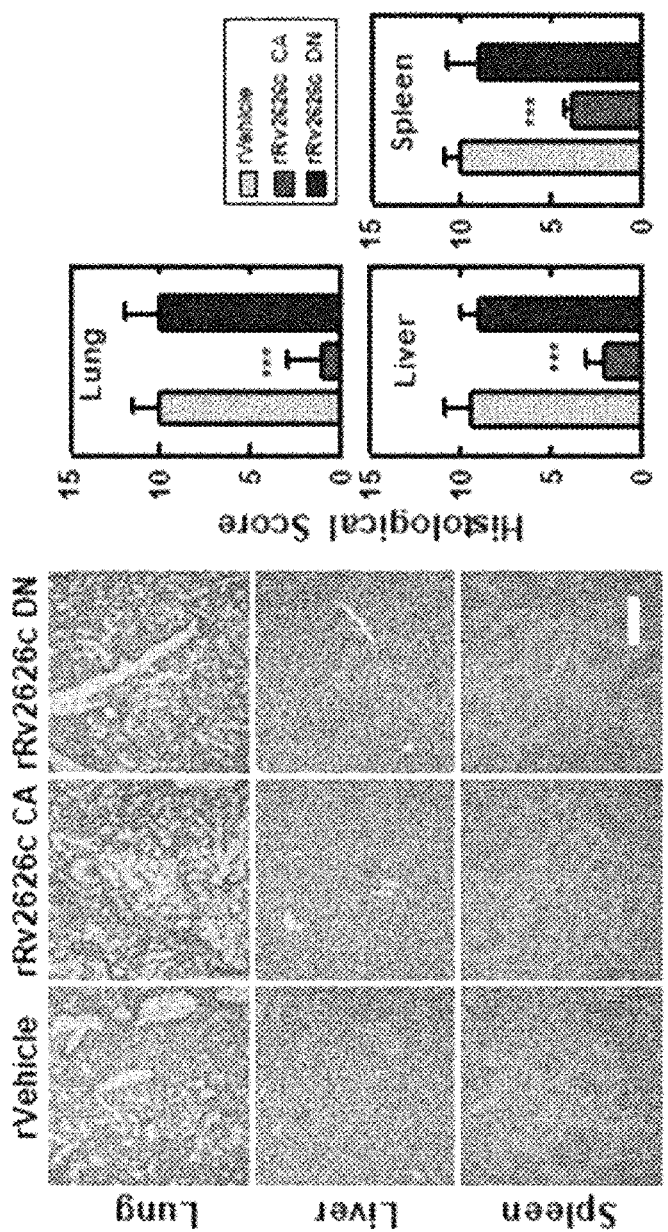
FIG. 18 is a result of performing biopsies after administration of different doses of rRv2626c-CA or Rv2626c-DN peptides to mice having induced sepsis.

Consistent with mortality data values, serum concentrations of pro-inflammatory cytokines such as TNF-α, IL-6, IL-1β, and IL-12p40 were significantly lowered in mice administered with rRv2626-CA. However, the concentration of IL-10 was significantly increased in mice administered with rRv2626c-CA (FIG. 17). This tendency was also similarly observed in H&E staining, and thus it was identified that in mice administered with rRv2626c-CA, the infiltration of immune cells was small and damage to the lungs, liver, and spleen was reduced (FIG. 18).

Next, it was identified whether rRv2626c-CA had in vivo pharmacological activity. In vivo detection of TRAF6 binding and its ubiquitination activity may be important for the evaluation of rRv2626c-CA in the discovery of candidate drugs for treating fatal inflammatory diseases.

Figure 19:
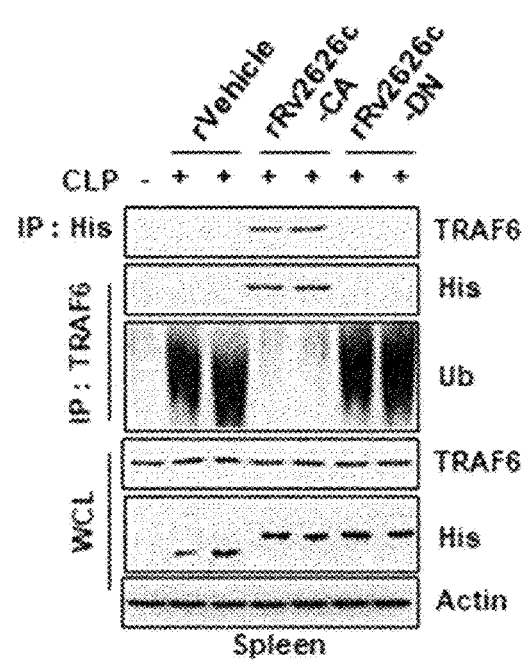
FIG. 19 is a result of identifying the binding to TRAF6 and the ubiquitination status of TRAF6 in splenocytes after administration of different doses of rRv2626c-CA or Rv2626c-DN peptides to mice having induced sepsis.
Figure 20:
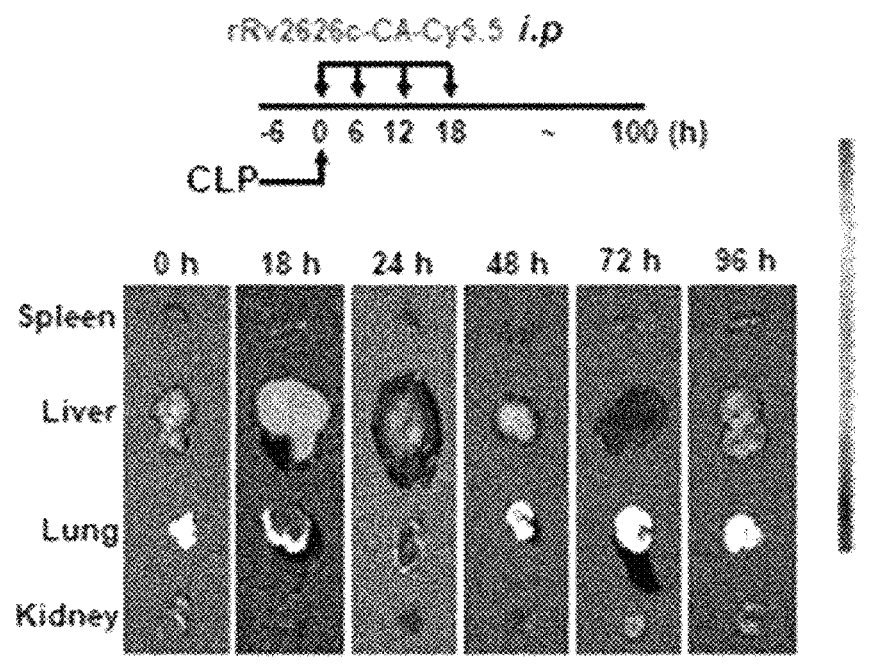
Figure 21:
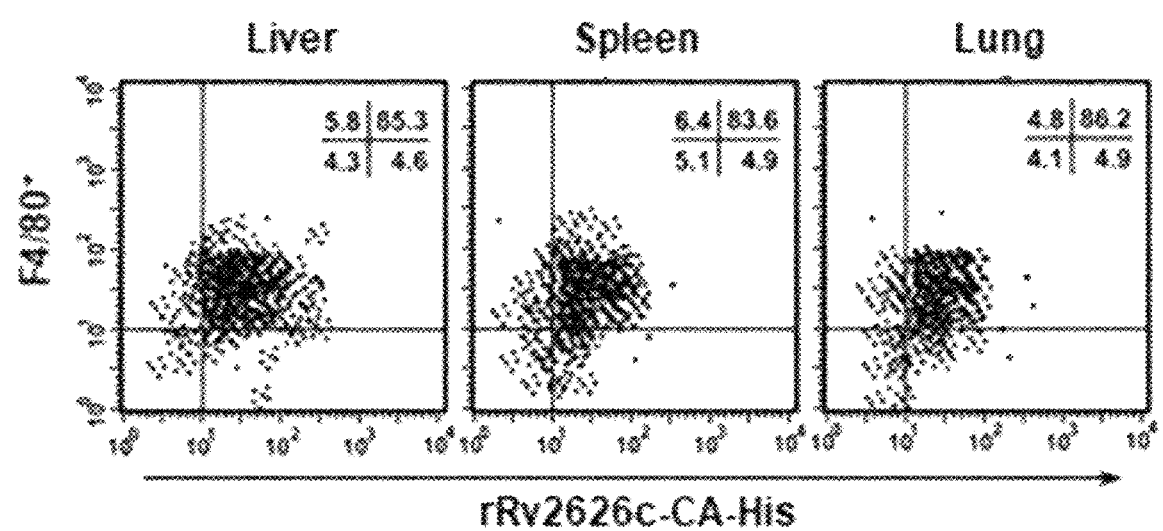
FIG. 21 is a result of identifying the cell types into which the rRv2626c-CA peptide is absorbed in the lungs, liver and spleen after administration of the rRv2626c-CA peptide to mice having induced sepsis.
Figure 22:
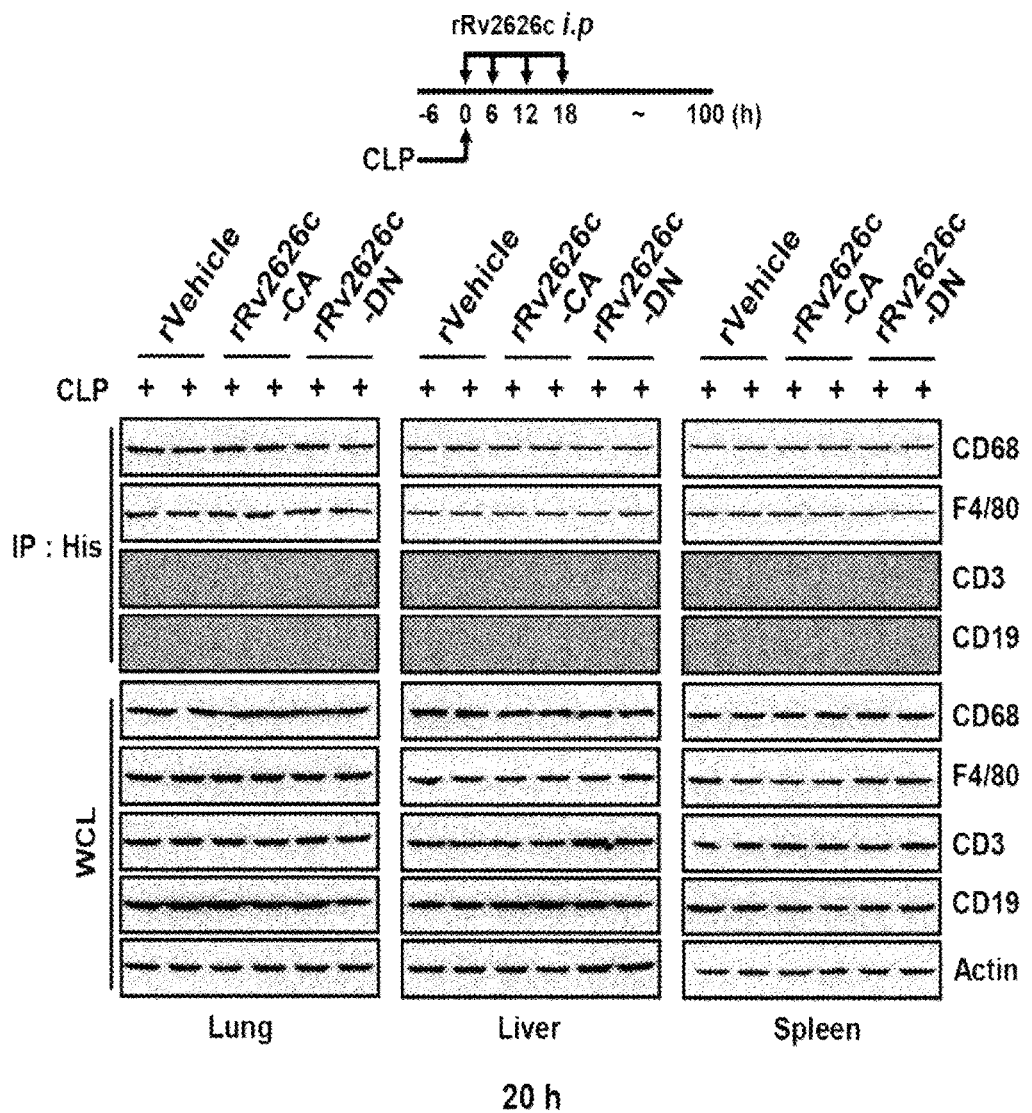
FIG. 22 is a result of identifying the cell types into which the rRv2626c-CA peptide is absorbed by immunoprecipitation in the lungs, liver and spleen after administration of the rRv2626c-CA peptide to mice having induced sepsis.

Consistent with in vitro data (FIG. 12), rRv2626c-CA interacted with TRAF6 and decreased the level of ubiquitination of TRAF6 in splenocytes (FIG. 19A). After administration of fluorescent rRv2626c-CA (rRv2626c-CA/Cy5.5), as a result of identifying the biodistribution and pharmacokinetics in the body of mice, rRv2626c-CA/Cy5.5 remained in the body for 72 hours, and the highest concentration was observed in the liver 18 and 24 hours after administration (FIG. 20). In addition, the tissue distribution of therapeutic rRv2626c-CA was in macrophages, not T cells and B cells of the lung, liver, and spleen (FIGS. 21 and 22). Taken together, these results suggest that rRv2626c-CA is not rapidly degraded in the body and circulates for a considerable period of time, and has potential as a therapeutic agent to ameliorate CLP-induced sepsis in macrophages.

7. rRv2626c-CA Enhances Bacterial Clearance.

Figure 23A:
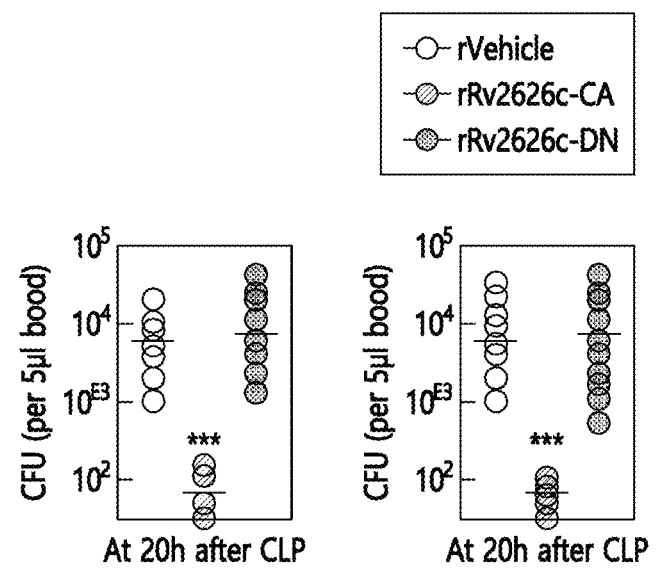
Figure 23B:
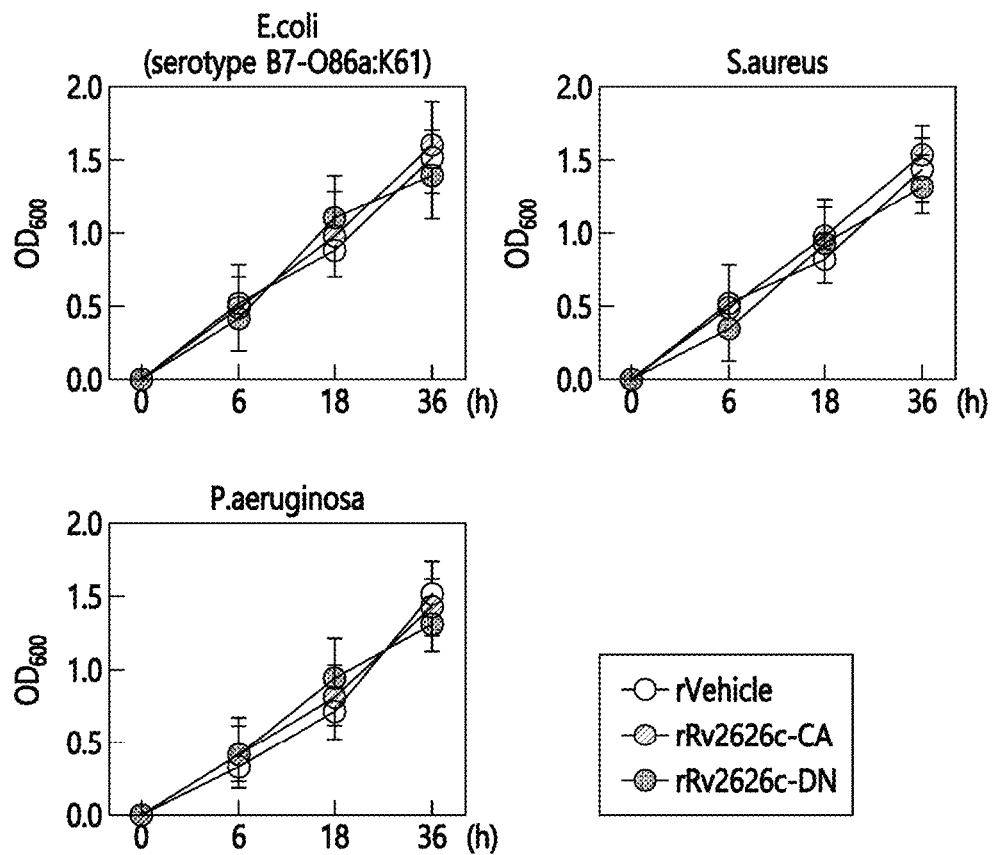
FIG. 23B is a result of identifying the degree of bacterial death in blood and peritoneal fluid after administration of the rRv2626c-CA peptide to mice induced to sepsis.

CLP-induced mortality is correlated with the number and amount of bacterial colonies in peripheral blood and peritoneal fluid. For identification, as a result of intraperitoneal injection of rRv2626c-CA to CLP mice, the number of bacterial colonies in both peritoneal fluid and blood was significantly reduced (FIG. 23A). However, a direct killing effect of rRv2626c-CA on bacteria was not observed (FIG. 23B).

Figure 24A:
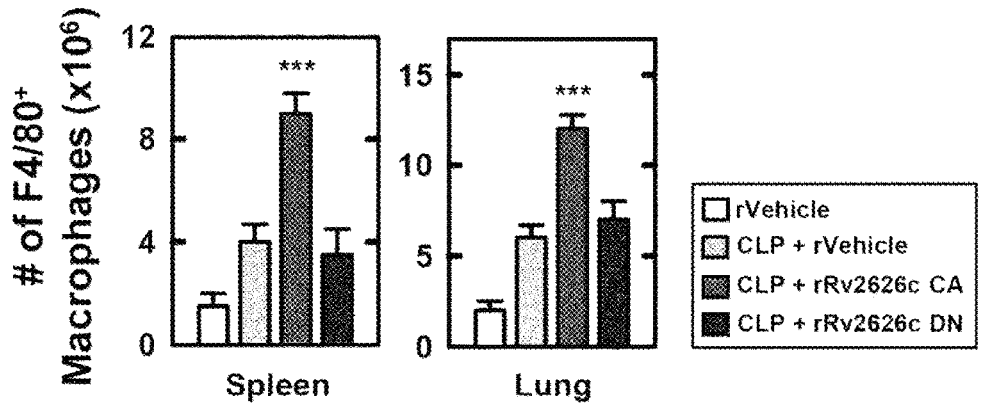
FIGS. 24A and 24B are results of identifying the number of immune cells recruited in the spleen and lung after administration of the rRv2626c-CA peptide to mice induced to sepsis.
Figure 24B:
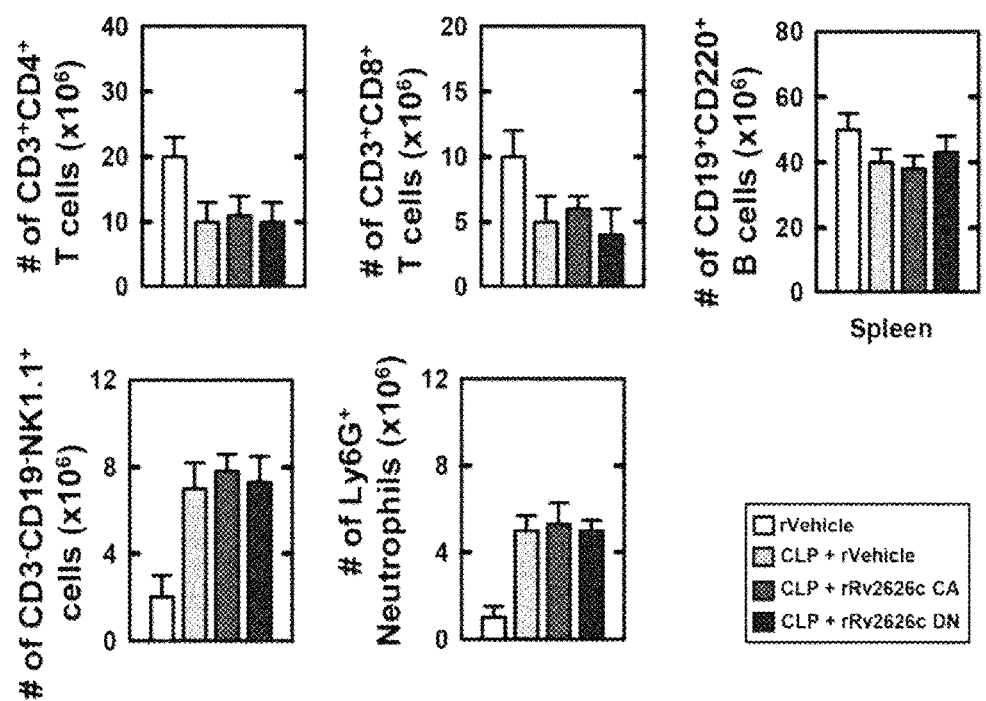
Figure 25:
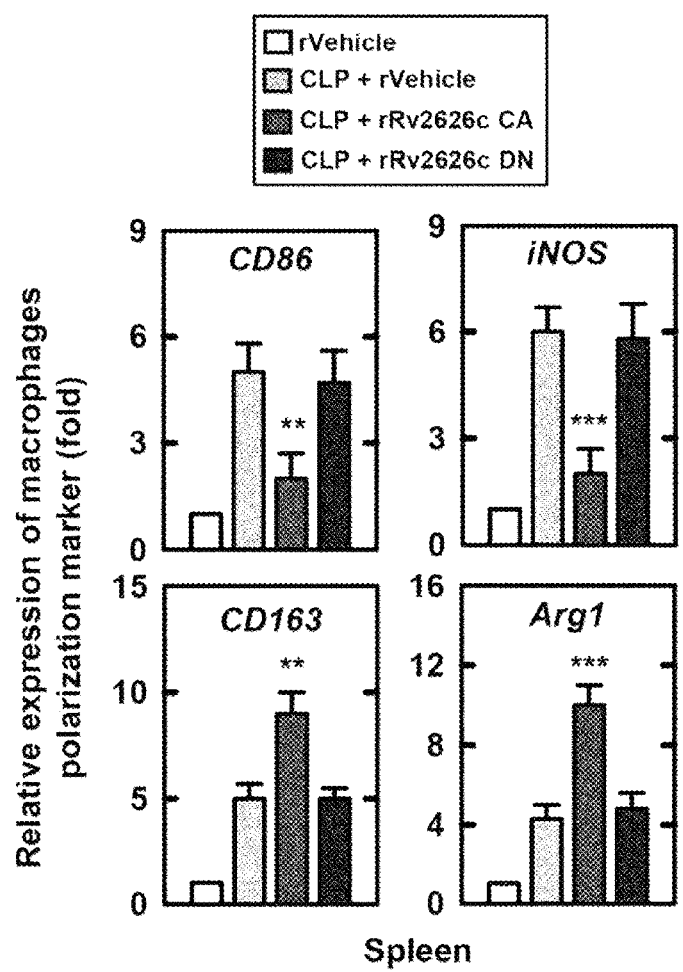
FIG. 25 is a result of identifying the types of macrophages recruited in the spleen and lungs after administration of the rRv2626c-CA peptide to mice induced to sepsis.

Since it has been reported that the bactericidal effect in the sepsis model is mainly mediated by the recruitment of neutrophils, it was investigated whether rRv2626c-CA increased the recruitment of immune cells in the sepsis model induced by CLP. In the rRv2626c-CA administration group, the number of macrophages recruited to the spleen and lungs increased significantly, but in the control group (rVehicle) and the rRv2626c-DN administration group, the number of macrophages did not increase (FIG. 24). In particular, macrophage recruitment by rRv2626c-CA increased type 2 macrophages and decreased type 1 macrophages (FIG. 25).

Figure 26:
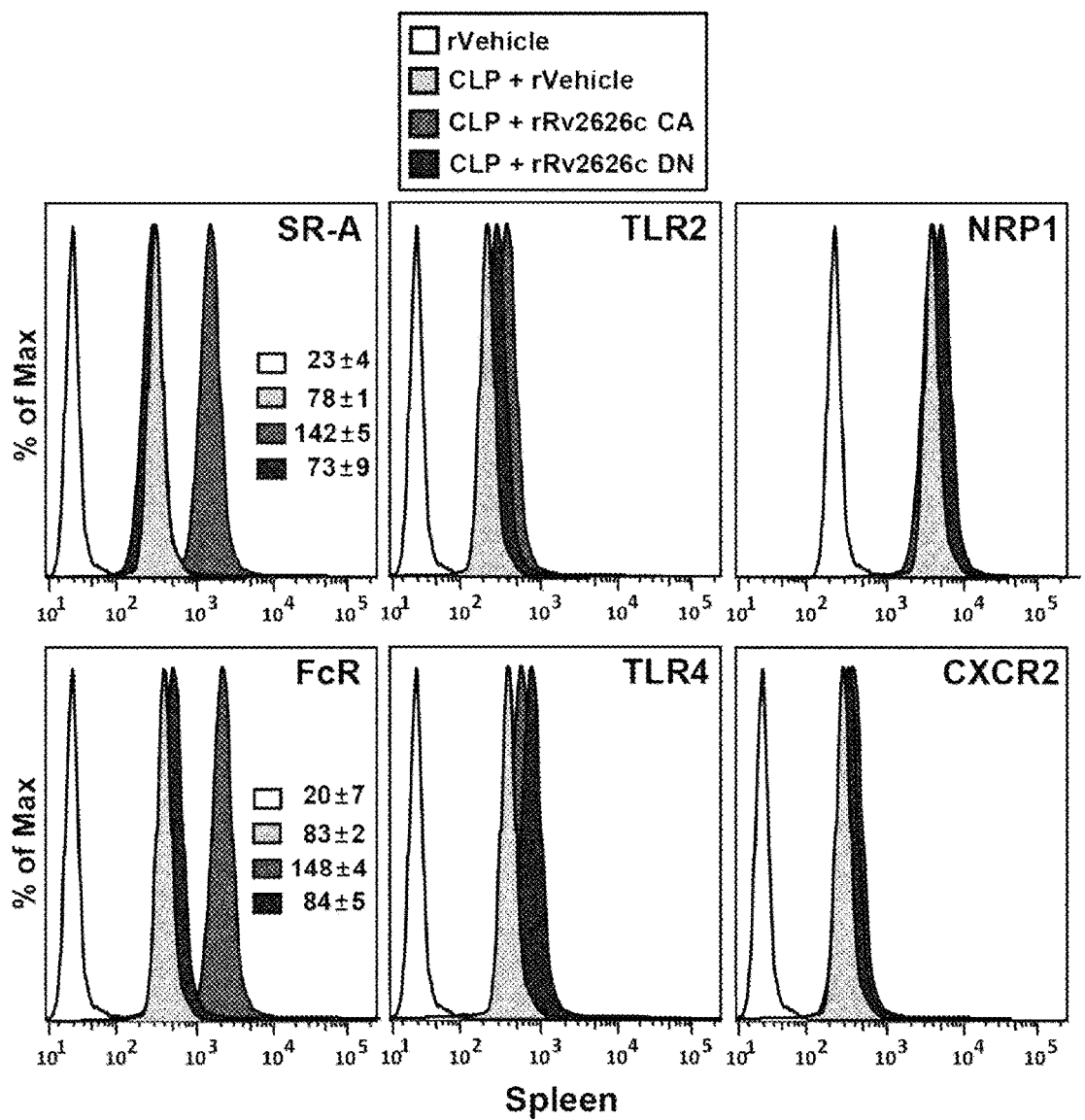
FIG. 26 is a result of identifying the expression levels of scavenger receptor-A (SR-A), Fc receptor (FcR), innate immune receptors (TLR2 and TLR4), and neutrophil receptors (Neuropilin-1 (NRP1) and CXCR2) after treatment of TRAF6 expressing macrophages with rRv2626c-CA.

In order to investigate how rRv2626c-CA contributes to macrophage recruitment, the expressions of phagocytic receptor-A (scavenger receptor-A, SR-A), Fc receptor, innate immune receptor (TLR2, TLR4), and neutrophil receptor (Neuropilin-1 and CXCR2) were identified in macrophages under the presence of TRAF6. As a result of identification, rRv2626c-CA increased the expressions of phagocytic receptor-A and Fc receptor (FIG. 26). These results strongly suggest the differentiation and recruitment of type 2 macrophages induced by rRv2626c-CA, phagocytosis, and antibacterial effect by enhanced phagocytosis.

Through the experimental results so far, the present inventors have identified the following facts: (1) Rv2626c C-terminal amino acid 123-131 sequences including two electrically charged residues were required for binding of Rv2626c and TRAF6. (2) Rv2626c inhibited TLR4 inflammatory signaling in macrophages by interacting with the RING domain of TRAF6 and inhibiting K63-linked polyubiquitination of TRAF6. (3) A tuftsin-binding Rv2626c peptide (123LPEHAIVQF131) targeting macrophages in vitro and in vivo was designed and expressed, and thus (4) newly developed rRv2626c-CA has significantly improved efficacy and selectivity compared to rRv2626c-WT. (5) rRv2626c-CA effectively eliminated sepsis-inducing bacteria by differentiation and recruitment of type 2 macrophages and enhanced phagocytosis. (6) rRv2626c-CA protected mice from infection by various microorganisms, which means that rRv2626c-CA of the present invention may be used as a therapeutic agent suitable for treating sepsis and other microorganism-mediated diseases.

Figure 27:
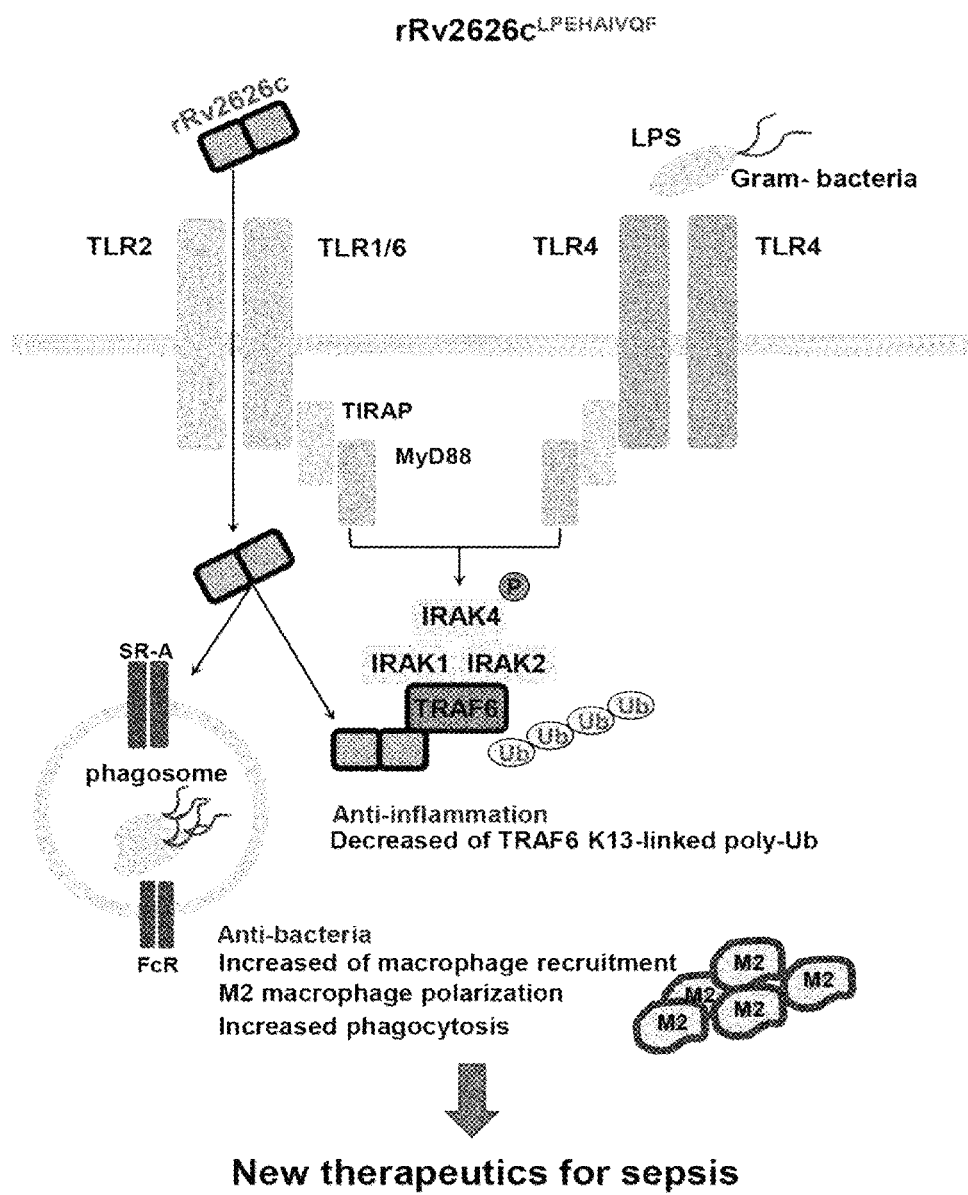
FIG. 27 schematically shows the regulatory mechanism of the TLR signaling pathway mediated by rRv2626c and the sepsis treatment mechanism therethrough.

FIG. 27 shows the regulatory mechanism of the TLR signaling pathway mediated by rRv2626c and the sepsis treatment mechanism therethrough.

Hereinbefore, the description of the present invention is for illustrative purposes only. It will be understood by those skilled in the technical field to which the present invention pertains that the present invention may be embodied in various other specific forms without departing from the technical ideas or essential characteristics of the present invention. Therefore, the disclosed examples should be considered in an illustrative rather than a restrictive perspective in all aspects.

What is claimed is:

1. A peptide of SEQ ID NO: 1 linked to a cell penetrating peptide, wherein the cell penetrating peptide is selected from the group consisting of HIV-TAT (SEQ ID NO: 3), TAT (SEQ ID NO: 5), dNP2 (SEQ ID NO: 6), VP22 (SEQ ID NO: 7), MPG (SEQ ID NO: 8), PEP-1 (SEQ ID NO: 9), EB1 (SEQ ID NO: 10), transportan (SEQ ID NO: 11), p-Antp (SEQ ID NO: 12), hCT (18-32) (SEQ ID NO: 13), KLA (SEQ ID NO: 14) and oligoarginine (SEQ ID NO: 15).

2. The peptide of claim 1 in which the amino acid sequence represented by SEQ ID NO: 1 is repeated 2 to 15 times.

3. The peptide of claim 1 further comprising a tuftsin peptide (SEQ ID NO: 2).

4. The peptide of claim 3, wherein the tuftsin peptide is included repeatedly from 1 to 20 times.

5. The peptide of claim 3, wherein the cell penetrating peptide, peptide of SEQ ID NO: 1, and tuftsin peptide, are sequentially linked.

6. The peptide of claim 3, wherein the cell penetrating peptide, tuftsin peptide, and peptide of SEQ ID NO: 1, are sequentially linked.

7. The peptide of claim 5, wherein each of the cell penetrating peptide, the amino acid sequence represented by SEQ ID NO: 1, and the tuftsin peptide are linked to one another with a peptide linker.

8. The peptide of claim 7, wherein the peptide linker is one selected from a group consisting of GG (SEQ ID NO: 16), (GGGGS)n (n=1-5) (SEQ ID NO: 17) and (EAAAK)n (n=1-5) (SEQ ID NO: 18).

9. A pharmaceutical composition comprising a peptide of claim 1 as an active ingredient.

10. A food composition comprising a peptide of claim 1 as an active ingredient.

11. A method for treating sepsis, comprising administering a peptide of claim 1 to a subject in need thereof.

* * * * *

SEQUENCE LISTING

<160> NUMBER OF SEQ ID NOS: 19

<210> SEQ ID NO 1
<211> LENGTH: 9
<212> TYPE: PRT
<213> ORGANISM: Mycobacterium tuberculosis

<400> SEQUENCE: 1

Leu Pro Glu His Ala Ile Val Gln Phe
1               5

<210> SEQ ID NO 2
<211> LENGTH: 4
<212> TYPE: PRT
<213> ORGANISM: Artificial Sequence
<220> FEATURE:
<223> OTHER INFORMATION: tuftsin

<400> SEQUENCE: 2

Thr Lys Pro Arg
1

<210> SEQ ID NO 3
<211> LENGTH: 12
<212> TYPE: PRT
<213> ORGANISM: Artificial Sequence
<220> FEATURE:
<223> OTHER INFORMATION: HIV-Tat

<400> SEQUENCE: 3

Gly Arg Lys Lys Arg Arg Gln Arg Arg Arg Pro Gln
1               5                   10

<210> SEQ ID NO 4
<211> LENGTH: 29
<212> TYPE: PRT
<213> ORGANISM: Artificial Sequence
<220> FEATURE:
<223> OTHER INFORMATION: CPP-GG-Tuftsin-GG-CBS2

<400> SEQUENCE: 4

Gly Arg Lys Lys Arg Arg Gln Arg Arg Arg Pro Gln Gly Gly Thr Lys
1               5                   10                  15

Pro Arg Gly Gly Leu Pro Glu His Ala Ile Val Gln Phe
            20                  25

<210> SEQ ID NO 5
<211> LENGTH: 11
<212> TYPE: PRT
<213> ORGANISM: Artificial Sequence
<220> FEATURE:
<223> OTHER INFORMATION: TAT

<400> SEQUENCE: 5

Tyr Gly Arg Lys Lys Arg Arg Gln Arg Arg Arg
1               5                   10

<210> SEQ ID NO 6
<211> LENGTH: 24
<212> TYPE: PRT
<213> ORGANISM: Artificial Sequence
<220> FEATURE:
<223> OTHER INFORMATION: dNP2

```
<400> SEQUENCE: 6

Lys Ile Lys Lys Val Lys Lys Gly Arg Lys Gly Ser Lys Ile Lys
1               5                   10                  15

Lys Val Lys Lys Lys Gly Arg Lys
            20

<210> SEQ ID NO 7
<211> LENGTH: 34
<212> TYPE: PRT
<213> ORGANISM: Artificial Sequence
<220> FEATURE:
<223> OTHER INFORMATION: VP22

<400> SEQUENCE: 7

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 8
<211> LENGTH: 27
<212> TYPE: PRT
<213> ORGANISM: Artificial Sequence
<220> FEATURE:
<223> OTHER INFORMATION: MPG

<400> SEQUENCE: 8

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 9
<211> LENGTH: 21
<212> TYPE: PRT
<213> ORGANISM: Artificial Sequence
<220> FEATURE:
<223> OTHER INFORMATION: PEP-1

<400> SEQUENCE: 9

Lys Glu Thr Trp Trp Glu Thr Trp Trp Thr Glu Trp Ser Gln Pro Lys
1               5                   10                  15

Lys Lys Arg Lys Cys
            20

<210> SEQ ID NO 10
<211> LENGTH: 23
<212> TYPE: PRT
<213> ORGANISM: Artificial Sequence
<220> FEATURE:
<223> OTHER INFORMATION: EB1

<400> SEQUENCE: 10

Leu Ile Lys Leu Trp Ser His Leu Ile His Ile Trp Phe Gln Asn Arg
1               5                   10                  15

Arg Leu Lys Trp Lys Lys Lys
            20

<210> SEQ ID NO 11
<211> LENGTH: 27
<212> TYPE: PRT
```

```
<213> ORGANISM: Artificial Sequence
<220> FEATURE:
<223> OTHER INFORMATION: transportan

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 12
<211> LENGTH: 16
<212> TYPE: PRT
<213> ORGANISM: Artificial Sequence
<220> FEATURE:
<223> OTHER INFORMATION: p-Antp

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: hCT(18-32)

<400> SEQUENCE: 13

Lys Phe His Thr Phe Pro Gln Thr Ala Ile Gly Val Gly Ala Pro
1               5                   10                  15

<210> SEQ ID NO 14
<211> LENGTH: 18
<212> TYPE: PRT
<213> ORGANISM: Artificial Sequence
<220> FEATURE:
<223> OTHER INFORMATION: KLA

<400> SEQUENCE: 14

Lys Leu Ala Leu Lys Leu Ala Leu Lys Ala Leu Lys Ala Ala Leu Lys
1               5                   10                  15

Leu Ala

<210> SEQ ID NO 15
<211> LENGTH: 8
<212> TYPE: PRT
<213> ORGANISM: Artificial Sequence
<220> FEATURE:
<223> OTHER INFORMATION: Oligoarginine

<400> SEQUENCE: 15

Arg Arg Arg Arg Arg Arg Arg Arg
1               5

<210> SEQ ID NO 16
<211> LENGTH: 2
<212> TYPE: PRT
<213> ORGANISM: Artificial Sequence
<220> FEATURE:
<223> OTHER INFORMATION: Peptide liker

<400> SEQUENCE: 16

Gly Gly
1
```

```
<210> SEQ ID NO 17
<211> LENGTH: 5
<212> TYPE: PRT
<213> ORGANISM: Artificial Sequence
<220> FEATURE:
<223> OTHER INFORMATION: Peptide liker

<400> SEQUENCE: 17

Gly Gly Gly Gly Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Peptide liker

<400> SEQUENCE: 18

Glu Ala Ala Ala Lys
1               5

<210> SEQ ID NO 19
<211> LENGTH: 9
<212> TYPE: PRT
<213> ORGANISM: Artificial Sequence
<220> FEATURE:
<223> OTHER INFORMATION: Rv2626c CBS2(123-131) MUTANT

<400> SEQUENCE: 19

Leu Pro Gln Gln Ala Ile Val Gln Phe
1               5
```